US012630641B2

(12) United States Patent     (10) Patent No.: US 12,630,641 B2
Bonifant                          (45) Date of Patent:     May 19, 2026

(54) COMPOSITIONS AND METHODS FOR T-CELL AND CYTOKINE ACTIVATION

(71) Applicant: The Regents of the University of Michigan, Ann Arbor, MI (US)

(72) Inventor: Challice Bonifant, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 18/359,624

(22) Filed: Jul. 26, 2023

(65) Prior Publication Data

US 2024/0247070 A1     Jul. 25, 2024

Related U.S. Application Data

(63) Continuation of application No. 16/358,253, filed on Mar. 19, 2019, now abandoned.

(60) Provisional application No. 62/644,900, filed on Mar. 19, 2018.

(51) Int. Cl.
| | |
|---|---|
| *C07K 16/28* | (2006.01) |
| *A61K 39/00* | (2006.01) |
| *A61K 40/11* | (2025.01) |
| *A61K 40/31* | (2025.01) |
| *A61K 40/42* | (2025.01) |
| *A61P 35/00* | (2006.01) |
| *A61P 35/02* | (2006.01) |
| *C07K 14/715* | (2006.01) |
| *A61K 38/00* | (2006.01) |

(52) U.S. Cl.
CPC .......... *C07K 16/2866* (2013.01); *A61K 40/11* (2025.01); *A61K 40/31* (2025.01); *A61K 40/4202* (2025.01); *A61K 40/4217* (2025.01); *A61P 35/00* (2018.01); *A61P 35/02* (2018.01); *C07K 14/7155* (2013.01); *C07K 16/2809* (2013.01); *C07K 16/2851* (2013.01); *A61K 38/00* (2013.01); *A61K 2039/505* (2013.01); *A61K 2239/38* (2023.05); *A61K 2239/48* (2023.05); *C07K 2317/31* (2013.01); *C07K 2317/53* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
CPC ............ C07K 16/2866; C07K 16/2851; C07K 16/2809; C07K 14/7155; C07K 2317/76; C07K 2317/622; C07K 2319/30; C07K 2319/03; C07K 2319/02; C07K 2317/31; C07K 2319/33; C07K 2317/53; A61K 35/17; A61K 2039/505; A61K 38/00; A61P 35/00; A61P 35/02
See application file for complete search history.

(56) References Cited

U.S. PATENT DOCUMENTS

| | | | |
|---|---|---|---|
| 4,946,778 A | 8/1990 | Ladner et al. | |
| 5,260,203 A | 11/1993 | Ladner et al. | |
| 9,765,156 B2 * | 9/2017 | June .................. | C07K 14/7051 |
| 2004/0043401 A1 * | 3/2004 | Sadelain .......... | C07K 14/70521 |
| | | | 435/325 |
| 2018/0021378 A1 | 1/2018 | Kang et al. | |
| 2018/0049412 A1 | 2/2018 | Shen | |

FOREIGN PATENT DOCUMENTS

| | | | | |
|---|---|---|---|---|
| WO | WO 88/01649 | 3/1988 | | |
| WO | WO 99/54440 | 10/1999 | | |
| WO | WO 2015/140268 | 9/2015 | | |
| WO | WO 2016/028896 | 2/2016 | | |
| WO | WO 2017049166 | 3/2017 | | |
| WO | WO-2017049166 A1 * | 3/2017 | ............ | A61K 35/17 |
| WO | WO 2017/172981 | 10/2017 | | |

OTHER PUBLICATIONS

Lloyd et al.Modelling the human immune response: performance of a 1011 human antibody repertoire against a broad panel of therapeutically relevant antigens. Protein Engineering, Design & Selection vol. 22 No. 3 pp. 159-168, 2009 (Year: 2009).*

International Search Report and Written Opinion for PCT/US19/22972. Mailed Jul. 24, 2019. 12 pages.

Extended European Search Report for PCT/2019022972. Mailed Dec. 3, 2021. 9 pages.

Alvarez-Vallina et al., Efficient discrimination between different densities of target antigen by tetracycline-regulatable T bodies. Hum Gene Ther. Mar. 1, 1999;10(4):559-63.

Appelbaum et al., Age and acute myeloid leukemia. Blood. May 1, 2006;107(9):3481-5.

Ausubel, Current Protocols in Molecular Biology, Green Publishing Associates and Wiley Interscience, N.Y. 1996. TOC only. 14 pages.

Bakker et al., C-type lectin-like molecule-1: a novel myeloid cell surface marker associated with acute myeloid leukemia. Cancer Res. Nov. 15, 2004;64(22):8443-50.

Bill et al., Mapping the CLEC12A expression on myeloid progenitors in normal bone marrow; implications for understanding CLEC12A-related cancer stem cell biology. J Cell Mol Med. Apr. 2018;22(4):2311-2318.

Bonifant et al., Advances in immunotherapy for pediatric acute myeloid leukemia. Expert Opin Biol Ther. Jan. 2018;18(1):51-63.

(Continued)

*Primary Examiner* — Daniel E Kolker
*Assistant Examiner* — Brian Hartnett
(74) *Attorney, Agent, or Firm* — David W. Staple; Casimir Jones, S.C.

(57)     ABSTRACT

Chimeric antigen receptors (CARs) are provided that comprise a CD123-specific antigen recognition domain and IL7Ra transmembrane and intracellular signaling domains (CD123/IL7Ra CARs). In particular embodiments, provided herein are engineered lymphocytes that express and display CD123/IL7Ra CARs, and methods of targeting CD123-positive leukemic cells and treating leukemias, such as acute myeloid leukemia (AML), therewith.

9 Claims, 24 Drawing Sheets

Specification includes a Sequence Listing.

(56)　　　　　References Cited

OTHER PUBLICATIONS

Bonifant et al., CD123-Engager T Cells as a Novel Immunotherapeutic for Acute Myeloid Leukemia. Mol Ther. Sep. 2, 20169;24(9):1615-26.

Bruhl, Depletion of CCR5-expressing cells with bispecific antibodies and chemokine toxins: a new strategy in the treatment of chronic inflammatory diseases and Hiv. J Immunol. Feb. 15, 2001;166(4):2420-6.

Chmielewski et al., T cell activation by antibody-like immunoreceptors: increase in affinity of the single-chain fragment domain above threshold does not increase T cell activation against antigen-positive target cells but decreases selectivity. J Immunol. Dec. 15, 2004;173(12):7647-53.

Cho et al., T cell receptor-dependent regulation of lipid rafts controls naive CD8+ T cell homeostasis. Immunity. Feb. 26, 2010;32(2):214-26.

Chothia et al., Canonical structures for the hypervariable regions of immunoglobulins. J Mol Biol. Aug. 20, 1987;196(4):901-17.

Chothia et al., Conformations of immunoglobulin hypervariable regions. Nature. Dec. 21-28, 1989;342(6252):877-83.

Deshpande et al., IL-7- and IL-15-mediated TCR sensitization enables T cell responses to self-antigens. J Immunol. Feb. 15, 2013;190(4):1416-23.

Du et al., New immunotoxins targeting CD123, a stem cell antigen on acute myeloid leukemia cells. J Immunother. Sep. 2007;30(6):607-13.

Fry et al., CD22-targeted Car T cells induce remission in B-ALL that is naive or resistant to CD19-targeted CAR immunotherapy. Nat Med. Jan. 2018;24(1):20-28.

Gill et al., Preclinical targeting of human acute myeloid leukemia and myeloablation using chimeric antigen receptor-modified T cells. Blood. Apr. 10, 2014;123(15):2343-54.

Hudson et al., Engineered antibodies. Nat Med. Jan. 2003;9(1):129-34.

Jiang et al., Distinct regions of the interleukin-7 receptor regulate different Bcl2 family members. Mol Cell Biol. Jul. 2004;24(14):6501-13.

Kloss et al., Combinatorial antigen recognition with balanced signaling promotes selective tumor eradication by engineered T cells. Nat Biotechnol. Jan. 2013;31(1):71-5.

Korpelainen et al., IL-3 receptor expression, regulation and function in cells of the vasculature. Immunol Cell Biol. Feb. 1996;74(1):1-7.

Korpelainen et al., Interferon-gamma upregulates interleukin-3 (IL-3) receptor expression in human endothelial cells and synergizes with IL-3 in stimulating major histocompatibility complex class II expression and cytokine production. Blood. Jul. 1, 1995;86(1):176-82.

Krawczyk et al., T-cell Activity against AML Improved by Dual-Targeted T Cells Stimulated through T-cell and IL7 Receptors. Cancer Immunol Res. Apr. 2019;7(4):683-692.

Kufer et al., Construction and biological activity of a recombinant bispecific single-chain antibody designed for therapy of minimal residual colorectal cancer. Cancer Immunol Immunother. Nov-Dec. 1997;45(3-4):193-7.

Laborda et al., Development of A Chimeric Antigen Receptor Targeting C-Type Lectin-Like Molecule-1 for Human Acute Myeloid Leukemia. Int J Mol Sci. Oct. 27, 2017;18(11):2259.

Lin et al., The role of shared receptor motifs and common Stat proteins in the generation of cytokine pleiotropy and redundancy by IL-2, IL-4, IL-7, IL-13, and IL-15. Immunity. Apr. 1995;2(4):331-9.

Lloyd et al. Modelling the human immune response: performance of a 1011 human antibody repertoire against a broad panel of therapeutically relevant antigens.Protein Engineering, Design & Selection, 2009;22(3);159-168.

Loffler et al., A recombinant bispecific single-chain antibody, CD19 x CD3, induces rapid and high lymphoma-directed cytotoxicity by unstimulated T lymphocytes. Blood. Mar. 15, 2000;95(6):2098-103.

Mack et al., A small bispecific antibody construct expressed as a functional single-chain molecule with high tumor cell cytotoxicity. Proc Natl Acad Sci U S A. Jul. 18, 1995;92(15):7021-5.

Mack et al., Biologic properties of a bispecific single-chain antibody directed against 17-1A (EpCAM) and CD3: tumor cell-dependent T cell stimulation and cytotoxic activity. J Immunol. Apr. 15, 1997;158(8):3965-70.

Maude et al., Chimeric antigen receptor T cells for sustained remissions in leukemia. N Engl J Med. Oct. 16, 2014;371(16):1507-17.

Mohammed et al., Improving Chimeric Antigen Receptor-Modified T Cell Function by Reversing the Immunosuppressive Tumor Microenvironment of Pancreatic Cancer. Mol Ther. Jan. 4, 2017;25(1):249-258.

Munoz et al., Interleukin-3 receptor alpha chain (CD123) is widely expressed in hematologic malignancies. Haematologica. Dec. 2001;86(12):1261-9.

Noordhuis et al. Targeting of CLEC12A In Acute Myeloid Leukemia by Antibody- Drug-Conjugates and Bispecific CLL-1xCD3 BITE Antibody. Blood 2010;116 (21): 2890.

O'Donnell et al., Acute Myeloid Leukemia, Version 3.2017, NCCN Clinical Practice Guidelines in Oncology. J Natl Compr Canc Netw. Jul. 2017;15(7):926-957.

Perna et al., Integrating Proteomics and Transcriptomics for Systematic Combinatorial Chimeric Antigen Receptor Therapy of AML. Cancer Cell. Oct. 9, 2017;32(4):506-519.e5.

Pizzitola et al., Chimeric antigen receptors against CD33/CD123 antigens efficiently target primary acute myeloid leukemia cells in vivo. Leukemia. Aug. 2014;28(8):1596-605.

Porter et al., Chimeric antigen receptor T cells persist and induce sustained remissions in relapsed refractory chronic lymphocytic leukemia. Sci Transl Med. Sep. 2, 2015;7(303):303ra139.

Rosenthal et al., IL-2 and IL-7 induce heterodimerization of STAT5 isoforms in human peripheral blood T lymphoblasts. Cell Immunol. Nov. 1, 1997;181(2):172-81.

Sadelain et al., The basic principles of chimeric antigen receptor design. Cancer Discov. Apr. 2013;3(4):388-98.

Shum et al., Constitutive Signaling from an Engineered IL7 Receptor Promotes Durable Tumor Elimination by Tumor-Redirected T Cells. Cancer Discov. Nov. 2017;7(11):1238-1247.

Stephan et al., T cell-encoded CD80 and 4-1BBL induce auto- and transcostimulation, resulting in potent tumor rejection. Nat Med. Dec. 2007;13(12):1440-9.

Surh et al., Homeostasis of naive and memory T cells. Immunity. Dec. 19, 2008;29(6):848-62.

Takada et al., Naive T cell homeostasis: from awareness of space to a sense of place. Nat Rev Immunol. Dec. 2009;9(12):823-32.

Tashiro et al., Treatment of Acute Myeloid Leukemia with T Cells Expressing Chimeric Antigen Receptors Directed to C-type Lectin-like Molecule 1. Mol Ther. Sep. 6, 2017;25(9):2202-2213.

Taussig et al., Hematopoietic stem cells express multiple myeloid markers: implications for the origin and targeted therapy of acute myeloid leukemia. Blood. Dec. 15, 2005;106(13):4086-92.

Turatti et al., Redirected activity of human antitumor chimeric immune receptors is governed by antigen and receptor expression levels and affinity of interaction. J Immunother. Oct. 2007;30(7):684-93.

Van Rhenen et al., The novel AML stem cell associated antigen CLL-1 aids in discrimination between normal and leukemic stem cells. Blood. Oct. 1, 2007;110(7):2659-66.

Velasquez et al., CD28 and 41BB Costimulation Enhances the Effector Function of CD19-Specific Engager T Cells. Cancer Immunol Res. Oct. 2017;5(10):860-870.

Velasquez et al., T cells expressing CD19-specific Engager Molecules for the Immunotherapy of CD19-positive Malignancies. Sci Rep. Jun. 3, 2016;6:27130.

Venkitaraman et al., Interleukin-7 induces the association of phosphatidylinositol 3-kinase with the alpha chain of the interleukin-7 receptor. Eur J Immunol. Sep. 1994;24(9):2168-74.

Vera et al., T lymphocytes redirected against the kappa light chain of human immunoglobulin efficiently kill mature B lymphocyte-derived malignant cells. Blood. Dec. 1, 2006;108(12):3890-7.

(56) References Cited

OTHER PUBLICATIONS

Wang et al., CAR-T cells targeting CLL-1 as an approach to treat acute myeloid leukemia. J Hematol Oncol. Jan. 10, 2018;11(1):7.

Zhao et al., Structural Design of Engineered Costimulation Determines Tumor Rejection Kinetics and Persistence of Car T Cells. Cancer Cell. Oct. 12, 2015;28(4):415-428.

Zhao et al., Targeting C-type lectin-like molecule-1 for antibody-mediated immunotherapy in acute myeloid leukemia. Haematologica. Jan. 2010;95(1):71-8.

Zwaan et al., Collaborative Efforts Driving Progress in Pediatric Acute Myeloid Leukemia. J Clin Oncol. Sep. 20, 2015;33(27):2949-62.

* cited by examiner

FIG. 3
- NT
- CD123.IL7Ra
- CLL-ENG
- Dual
- Bicistronic
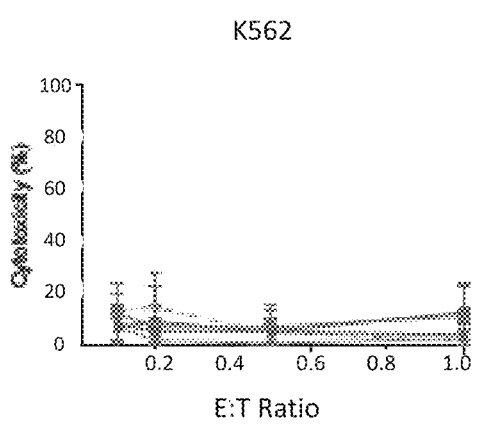
K562
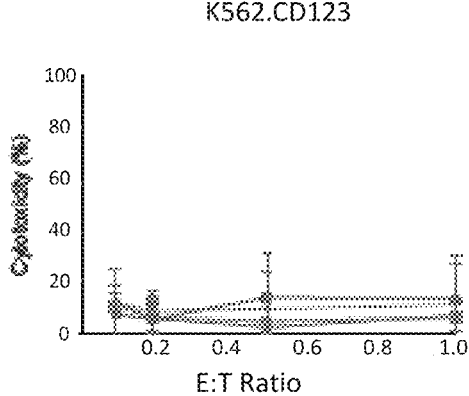
K562.CD123
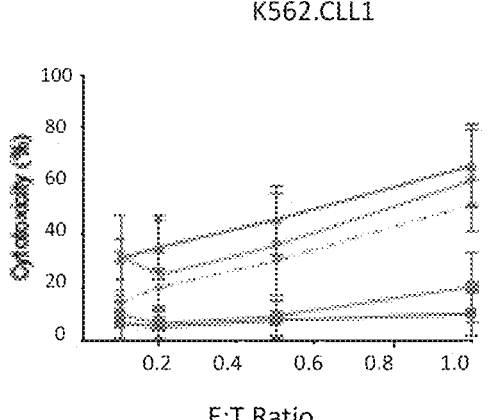
K562.CLL1
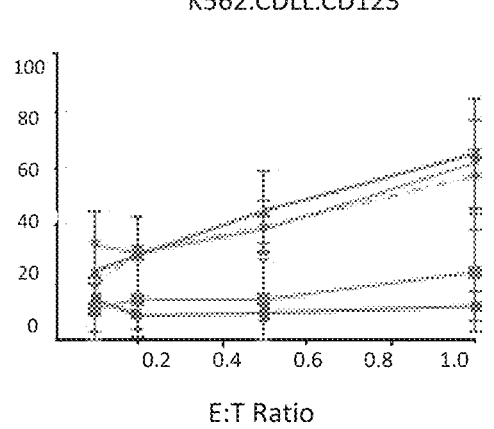
K562.CDLL.CD123

FIG. 4
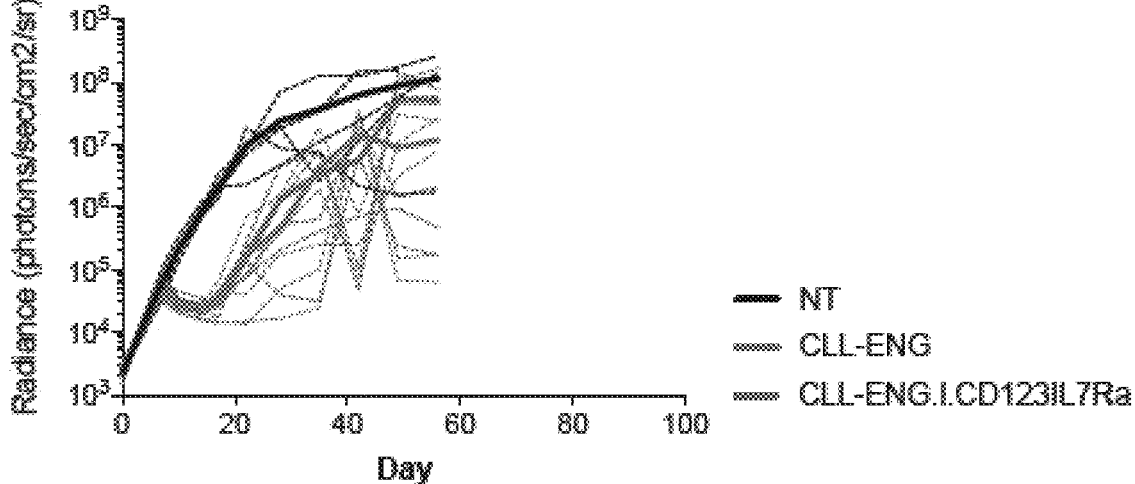
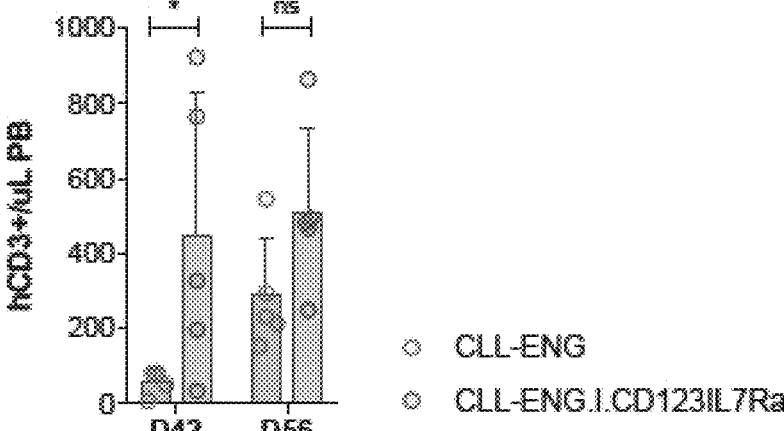

FIG. 6 A-D
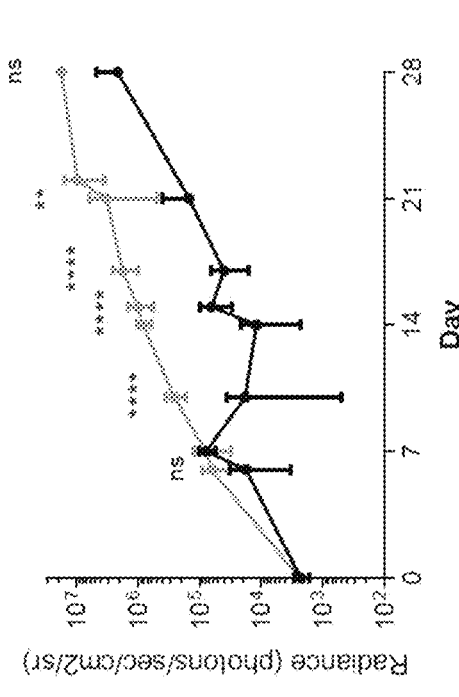
B.
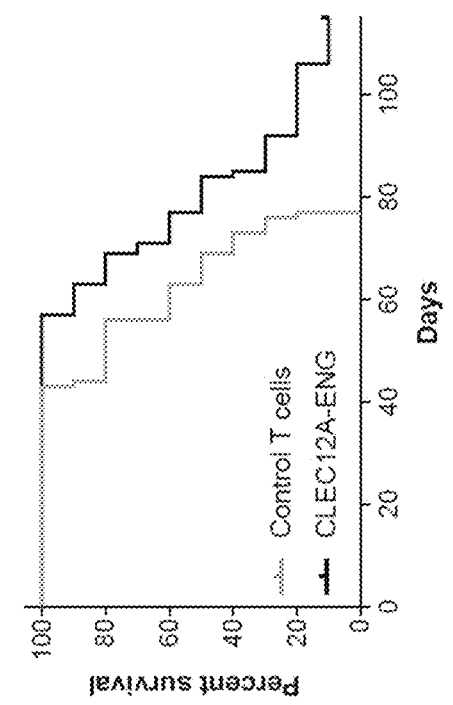
A.
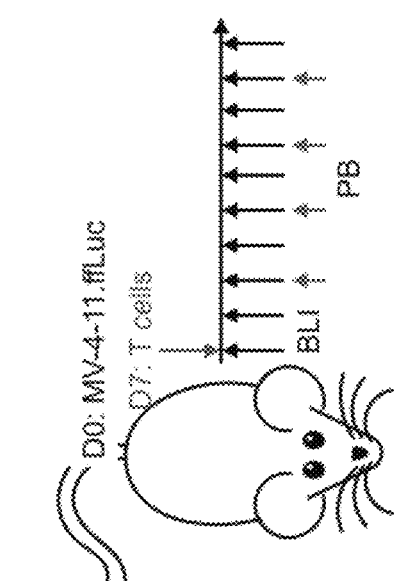
C.
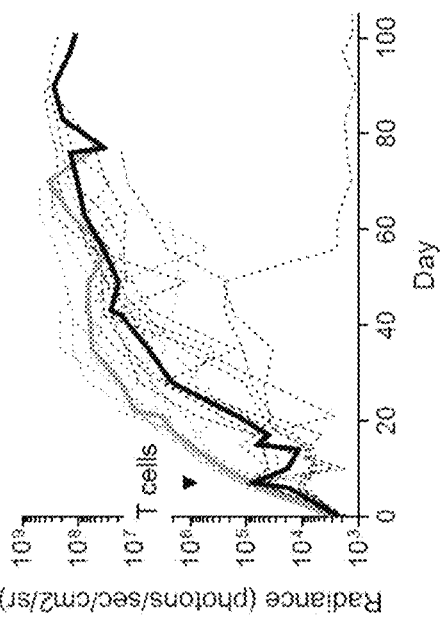
D.

FIG. 7 A-D
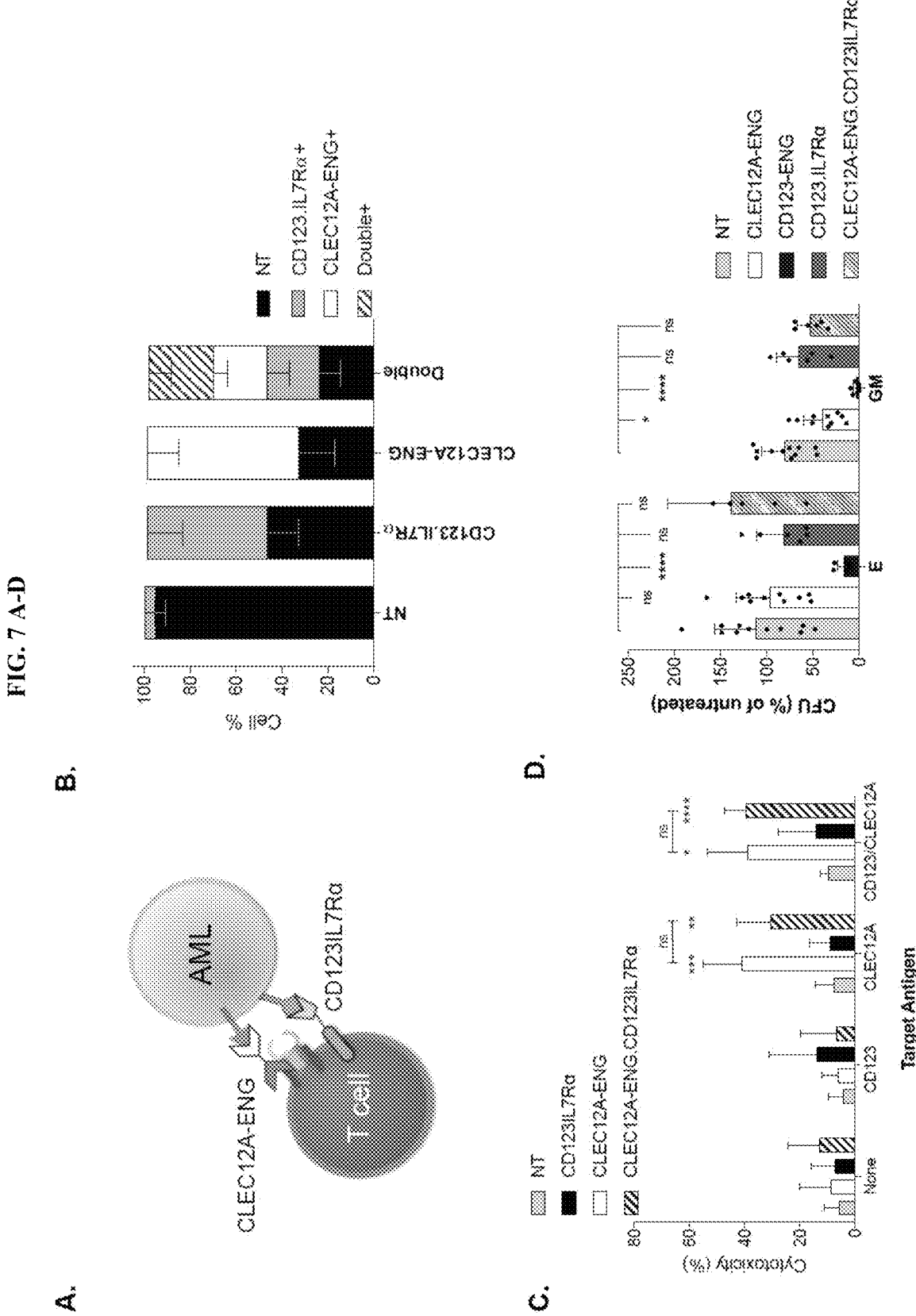

C. CD123IL7Rα (ΔBox1)

D. CD123IL7Rα (Y449F)

E. CLEC12A-ENG

F. CLEC12A-ENG. CD123IL7Rα

G. CLEC12A-ENG. CD123IL7Rα (ΔBox1)

H. CLEC12A-ENG. CD123IL7Rα (Y449F)

FIG. 11

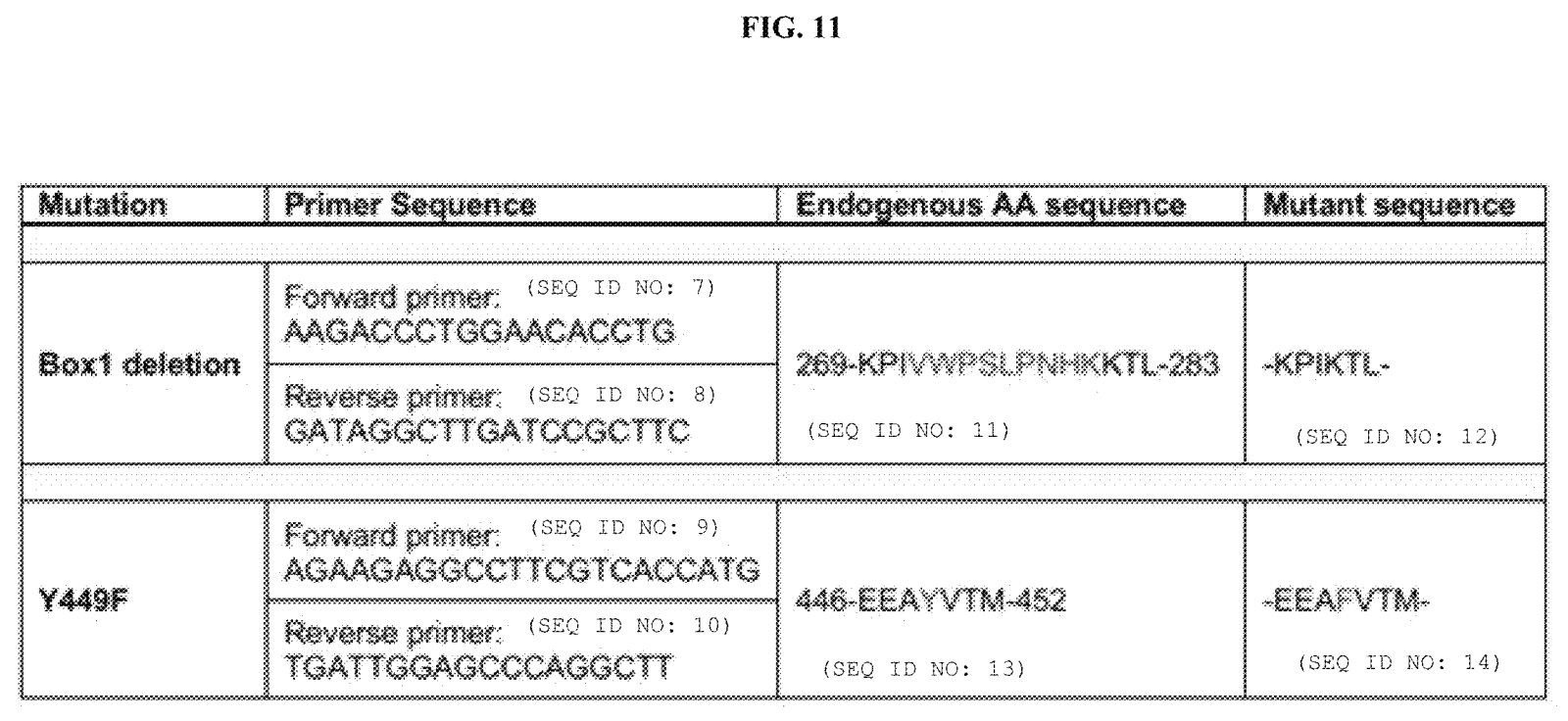

| Mutation | Primer Sequence | Endogenous AA sequence | Mutant sequence |
|---|---|---|---|
| Box1 deletion | Forward primer: (SEQ ID NO: 7) AGACCCTGGAACACCTG<br><br>Reverse primer: (SEQ ID NO: 8) GATAGGCTTGATCGGCTTC | 269-KPIVWPSLPNHKKTL-283<br><br>(SEQ ID NO: 11) | -KPIKTL-<br><br>(SEQ ID NO: 12) |
| Y449F | Forward primer: (SEQ ID NO: 9) AGAAGAGGCCTTCGTCACCATG<br><br>Reverse primer: (SEQ ID NO: 10) TGATTGGAGCCCAGGCTT | 446-EEAYVTM-452<br><br>(SEQ ID NO: 13) | -EEAFVTM-<br><br>(SEQ ID NO: 14) |

FIG. 12 A-B
A.
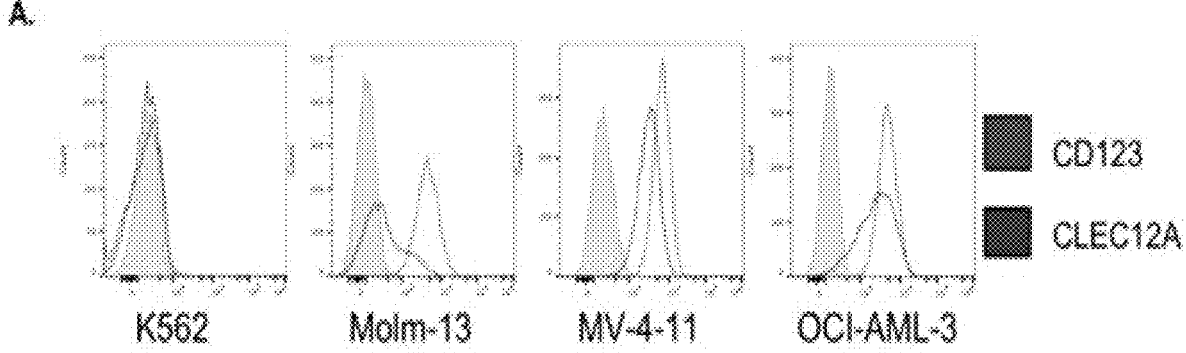
B.
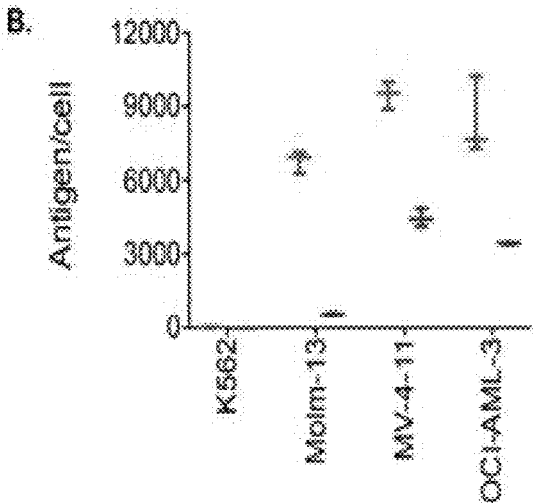

FIG. 15 A-B
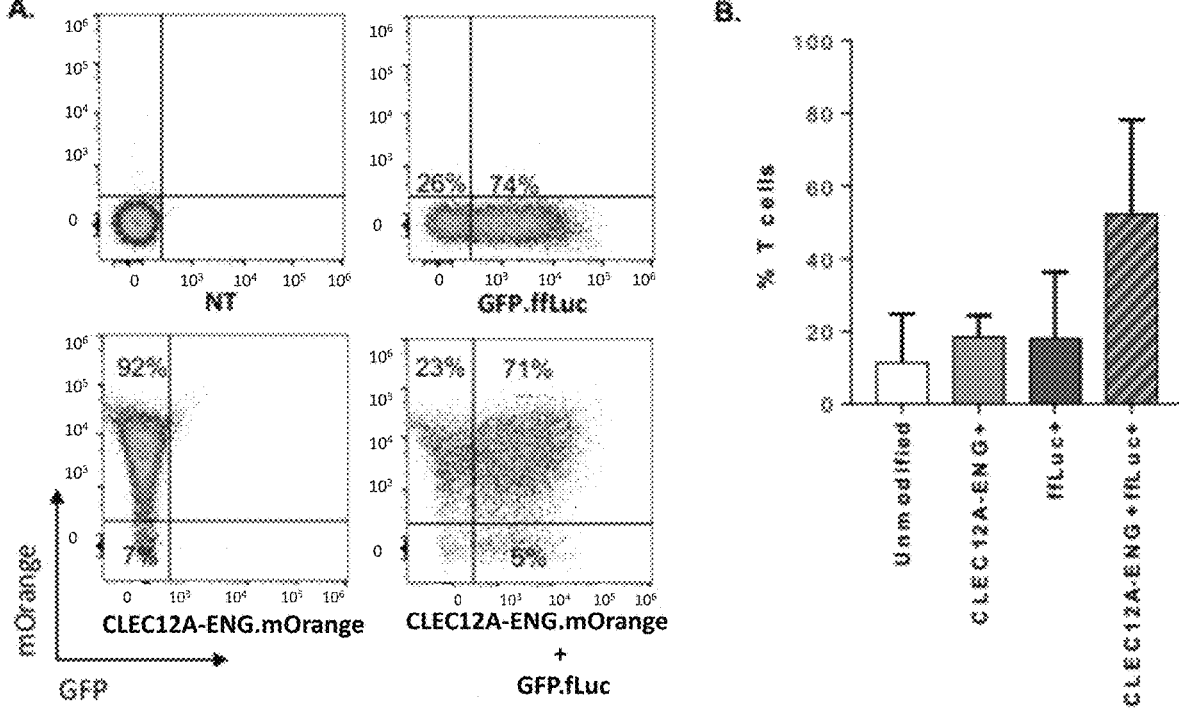

FIG. 16 A-D
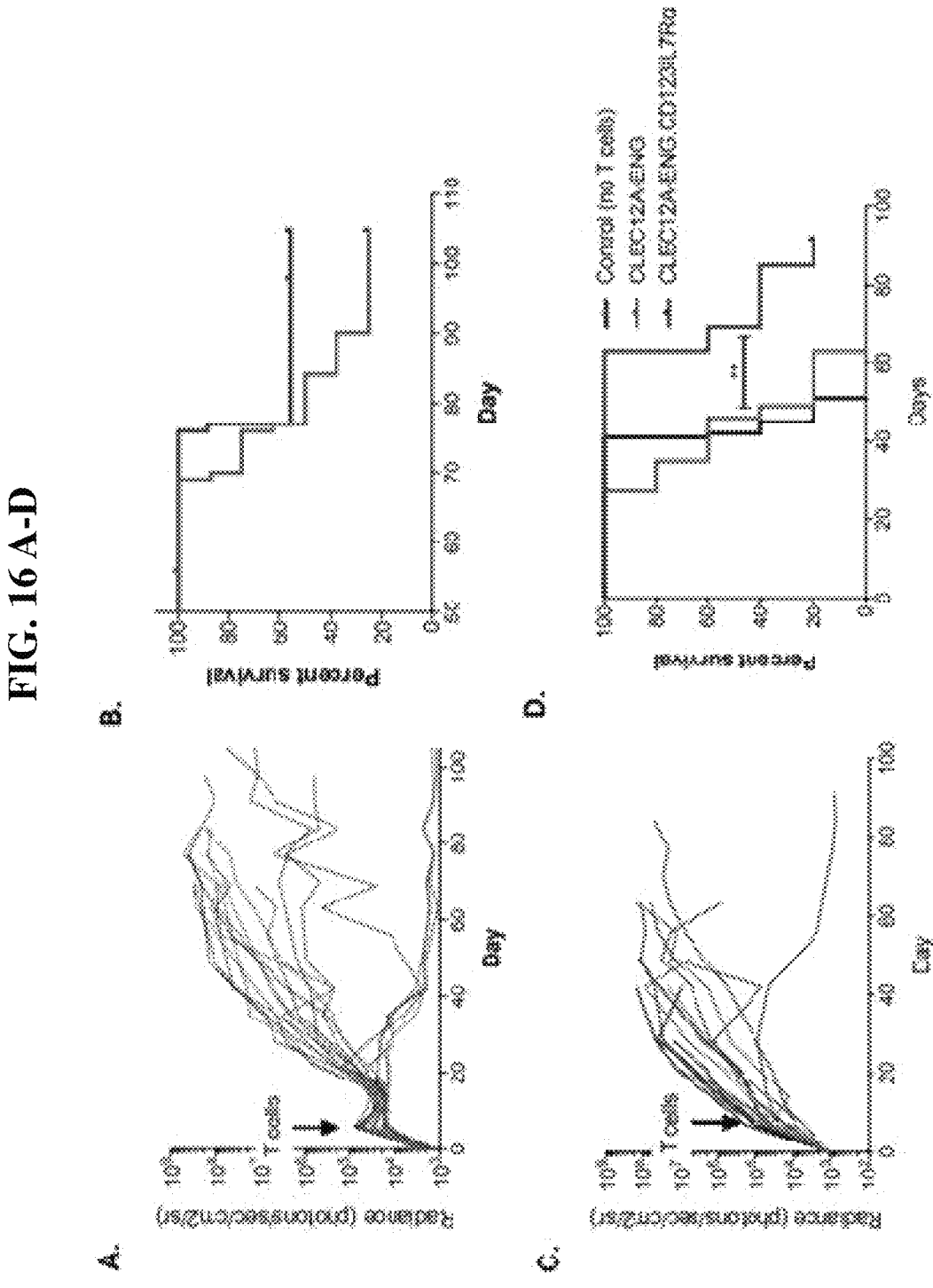

FIG. 17 A-B
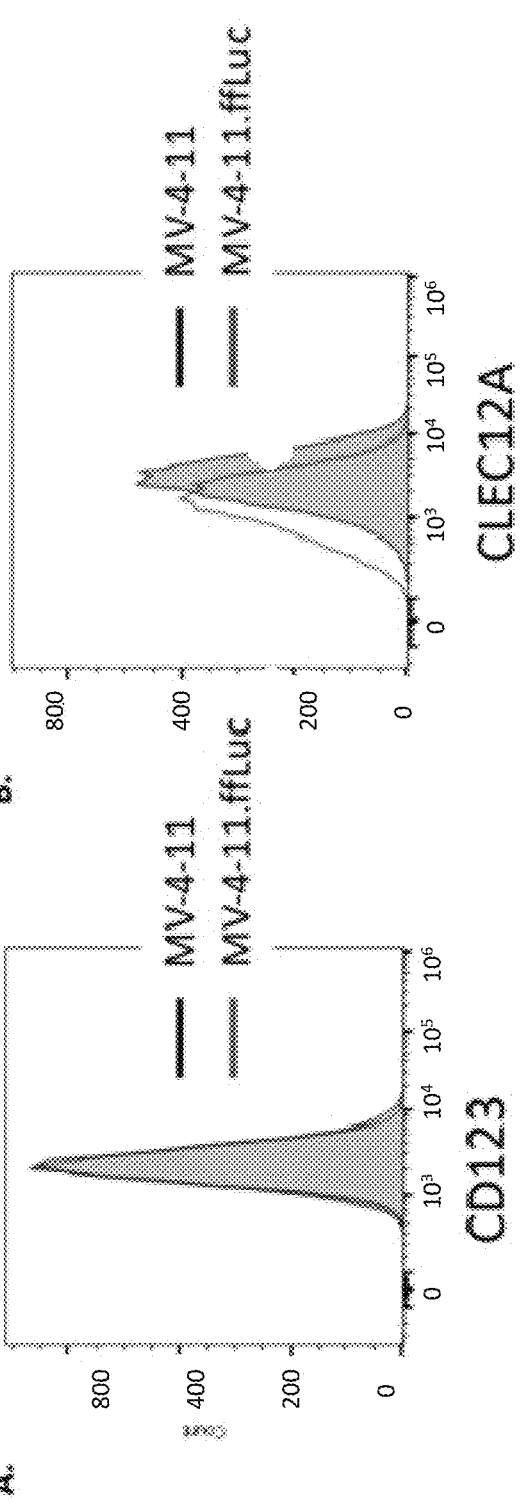

COMPOSITIONS AND METHODS FOR T-CELL AND CYTOKINE ACTIVATION

CROSS-REFERENCE TO RELATED APPLICATIONS

The present invention is a continuation of U.S. patent application Ser. No. 16/358,253, filed on Mar. 19, 2019, which claims priority to U.S. Provisional Patent Application 62/644,900, filed Mar. 19, 2018, which is incorporated by reference in its entirety.

SEQUENCE LISTING

The text of the computer readable sequence listing filed herewith, titled "35682-303_SEQUENCE_LISTING", created Jul. 26, 2023, having a file size of 8,208 bytes, is hereby incorporated by reference in its entirety.

FIELD

Chimeric antigen receptors (CARs) are provided that comprise a CD123-specific antigen recognition domain and IL7Ra transmembrane and intracellular signaling domains (CD123/IL7Ra CARs). In particular embodiments, provided herein are engineered lymphocytes that express and display CD123/IL7Ra CARs, and methods of targeting CD123-positive leukemic cells and treating leukemias, such as acute myeloid leukemia (AML), therewith.

BACKGROUND

AML, with a cure rate of less than 30% for high risk and relapsed disease, is a cancer in need of new therapeutic strategies to impact patient survival. Despite the dismal prognosis, the mortality rate due to acute myeloid leukemia (AML) has remained relatively unchanged for the last four decades. The standard chemotherapy regimen has not been altered in nearly 40 years, in part because of the difficulty in specifically targeting leukemic myeloblasts while sparing normal tissue.

SUMMARY

Chimeric antigen receptors (CARs) are provided that comprise a CD123-specific antigen recognition domain and IL7Ra transmembrane and intracellular signaling domains (CD123/IL7Ra CARs). In particular embodiments, provided herein are engineered lymphocytes that express and display CD123/IL7Ra CARs, and methods of targeting CD123-positive leukemic cells and treating leukemias, such as acute myeloid leukemia (AML), therewith.

In some embodiments, provided herein are polypeptides comprising a chimeric antigen receptor (CAR), the CAR comprising an anti-CD123 antigen-recognition domain, an IL7Ra transmembrane domain, and an IL7Ra intracellular signaling domain. In some embodiments, the antigen-recognition domain is an antibody fragment. In some embodiments, the antigen-recognition domain is a single chain variable fragment (scFv). In some embodiments, polypeptides further comprise a hinge domain between the antigen-recognition domain and transmembrane domain. In some embodiments, polypeptides further comprise one or more linker segments between domains.

In some embodiments, provided herein are engineered lymphocytes expressing a chimeric antigen receptor (CAR) described herein (e.g., a CAR comprising an anti-CD123 antigen-recognition domain, an IL7Ra transmembrane domain, and an IL7Ra intracellular signaling domain). In some embodiments, the lymphocyte is a T cell. In some embodiments, the lymphocyte is an NK cell. In some embodiments, the lymphocyte further expresses a bispecific engager molecule comprising: (a) an antigen-recognition domain that specifically binds to C-type lectin-like molecule-1 (CLL-1); and (b) an activation domain that interacts with a portion of T cell receptor (TCR) to induce an immunomodulatory signal. In some embodiments, the antigen-recognition domain of the bispecific engager is an antibody fragment. In some embodiments, the antigen-recognition domain is a single chain variable fragment (scFv). In some embodiments, the activation domain is an antibody fragment. In some embodiments, the activation domain is a single chain variable fragment (scFv). In some embodiments, the activation domain is an anti-CD3 antibody fragment. In some embodiments, the activation domain and antigen-recognition domain are single chain variable fragments tethered to each other by a linker domain.

In some embodiments, provided herein are engineered lymphocytes comprising: (a) a first polynucleotide sequence encoding bispecific engager molecule that comprises a CLL-1 antigen-recognition domain capable of binding a CLL-1 antigen and an activation domain capable of binding a molecule moiety displayed on T cells that activates an immunomodulatory signal upon binding; and (b) a second polynucleotide sequence encoding a chimeric antigen receptor (CAR) that comprises a CD123 antigen-recognition domain capable of binding a CD123 antigen, a IL7Ra transmembrane domain, and a IL7Ra intracellular signaling domain. In some embodiments, the first polynucleotide sequence and the second polynucleotide sequence are portions of a single nucleic acid or vector. In some embodiments, the first polynucleotide sequence and the second polynucleotide sequence are portions of separate nucleic acids or vectors. In some embodiments, the lymphocyte is a T cell. In some embodiments, the lymphocyte is an NK cell.

In some embodiments, provided herein are methods of treating a disease or condition comprising administering the engineered lymphocytes described herein to a subject. In some embodiments, the subject suffers from cancer. In some embodiments, the subject suffers from leukemia. In some embodiments, the subject suffers from acute myeloid leukemia (AML).

In some embodiments, provided herein is the use of an engineered lymphocyte described herein for the treatment of a disease or condition. In some embodiments, the disease or condition is cancer. In some embodiments, the disease or condition is leukemia. In some embodiments, the disease or condition is acute myeloid leukemia (AML).

BRIEF DESCRIPTION OF THE DRAWINGS

FIG. 3. Graphs depicting cytotoxicity of T cells expressing CD123/IL7Ra CARs, CLL/CD3 ENG, both, both bicistronically, or neither in the presence of K562 cells displaying CD123, CLL, both, or neither.

FIG. 4. Graphs depicting persistence in mice of T cells expressing CD123/IL7Ra CARs, CLL/CD3 ENGs, or neither.

FIG. 6, Panels A-D. CLEC12A-ENG T cells exhibit antitumor efficacy in vivo. A. Schematic of MV-4-11 Xenograft model. NSG mice were engrafted with 1e6 MV-4-11.ffLuc i.v. on Day 0. On Day 7, 10e6 T cells (Control or CLEC12A-ENG) were administered. Leukemia was followed with bioluminescent imaging (BLI) and T cells tracked in peripheral blood every 2 weeks beginning on day 21. B and C. Quantitation of sequential BLI of mice (n=5 mice per group per experiment, two independent experiments, with a different T-cell donor for each experiment). (B) Leukemia burden over first 28 days between control (gray line) and CLEC12AENG-treated (black line) mice. (C) Extended BLI data from (B). Dashed lines represent each individual mouse, solid lines are average BLI of group. Gray lines, control mice; black lines, treated mice. D. Kaplan-Meier survival analysis, Median survival: Control T cells—66 days, CLEC12A-ENG T cells—80.5 days. p=0.01.

FIG. 7, Panels A-D. Coupling of CD123 recognition to IL7R signaling does not cause hematopoietic toxicity. A. Schematic of CLEC12A-ENG.CD123IL7Rα T-cell targeting of CLL1+CD123+ AML. B. Transduction efficiency of NT, singly modified CD123.IL7Ra, CLEC12A-ENG, and dual modified CLEC12A-ENG.CD123IL7Rα T cells. (n=4 independent T-cell donors). C. Cytotoxicity of T cells versus CLEC12A+, CD123+, or CLEC12A+CD123+ target cells. E:T Ratio:1:5. Significant differences measured in comparison to NT T cells. D. Cfu assays performed with 5:1 ratio of T cells to BMMCs. CD123-ENG T cells used as positive control. (n=5 BMMC donors, 4 T-cell donors. Data normalized to "no T cell" conditions, differences relative to NT T-cell control.

FIGS. 8A-C. Expression of CD123.IL7Rα stimulates enhanced T-cell activation. A. Schematic of mutant IL7Rα receptors. B. STAT5 activation demonstrated downstream of IL7Rα receptor in engineered T cells. Cells were starved of cytokine, lysed, and Western blot performed. Densitometry analysis calculated as p-STAT5/STAT5. (n=1-2 donors of each T-cell type) C. Representative Western blot for phospho-STAT5 and STAT5. Positive control (+): NT T cells treated with 10 ng/mL rhIL7 for 30 minutes prior to lysis.

FIG. 11. Primer sequences used to generate IL7Rα mutants. Forward and reverse primers used for mutagenesis are displayed. Numbering reflects NCBI Reference Sequence: NP_002176.2 (Interleukin-7 receptor subunit alpha precursor) amino acid sequence.

FIG. 12, Panels A-B. CLEC12A and CD123 expression on leukemia cell lines. A. FACS histograms of CLEC12A and CD123 expression (K562, Molm-13, MV-4-11, OCI-AML-3) on human leukemia cell lines. B. Quantification of antigen density performed using QuantiBrite beads (BD Biosciences). Data expressed as median(range), n=3. CD123—K562: 32.4 (0.2-42.3), Molm-13: 6937.8(6255.4-7144.6), MV-4-11: 9545.7(8869.4-9991.1), OCI-AML-3: 7653.9(7292.4-10235.1); CLEC12A—K562: 0.0(0.0-0.0), Molm-13: 552.8(552.8-578.1), MV-4-11: 4412.1(4113.7-4848.9), OCI-AML-3: 3454.2(3410.8-3462.3).

FIG. 15, Panels A-B. Co-expression of GFP.ffLuc and CLEC12A-ENG.mO in primary T cells. A. Representative FACS analysis of T cells transduced with retroviral vectors encoding a GFP.ffLuc fusion protein and/or CLEC12A-ENG.IRES.mOrange. B. Percentages of each T cell population in culture (n=2 independent T cell donors).

FIG. 16, Panels A-D. CD123.IL7Rα expressing T cells have improved in vivo anti-leukemia control. A. Quantitation of sequential bioluminescent imaging of mice (n=8-10 mice each group) engrafted with 1e6 MV4-11.ffLuc on D0 and treated with 10e6 T cells i.v. on D7. B. Kaplan-Meier survival analysis, Median survival: CLEC12A-ENG—80.5 days, CLEC12A-ENG.CD123.IL7Rα—91 days. All mice dead in CLEC12A-ENG group died with high leukemic burden. C. Serial bioluminescent imaging data of alternate CLEC12A+/CD123+ xenograft model. Mice were injected via tail vein with 1e6 OCI-AML-3.ffLuc cells on D0 and treated with indicated T cells on D7. Untreated mice served as a control. (n=5 mice each group) D. Kaplan-Meier survival analysis, Median survival: No T cells—42 days, CLEC12A-ENG—46 days, CLEC12AENG.CD123.IL7Rα—69 days.

FIG. 17, Panels A-B. MV-4-11 and MV-4-11.ffLuc have different levels of CLEC12A expression. A. MV-4-11 and MV-4-11.ffLuc stained with CD123-PE antibody (BD Biosciences, Clone 7G3). B. MV-4-11 and MV-4-11.ffLuc stained with CLEC12A− Alexa647 antibody (BD Biosciences, Clone 50C1).

DEFINITIONS

Figure 1:
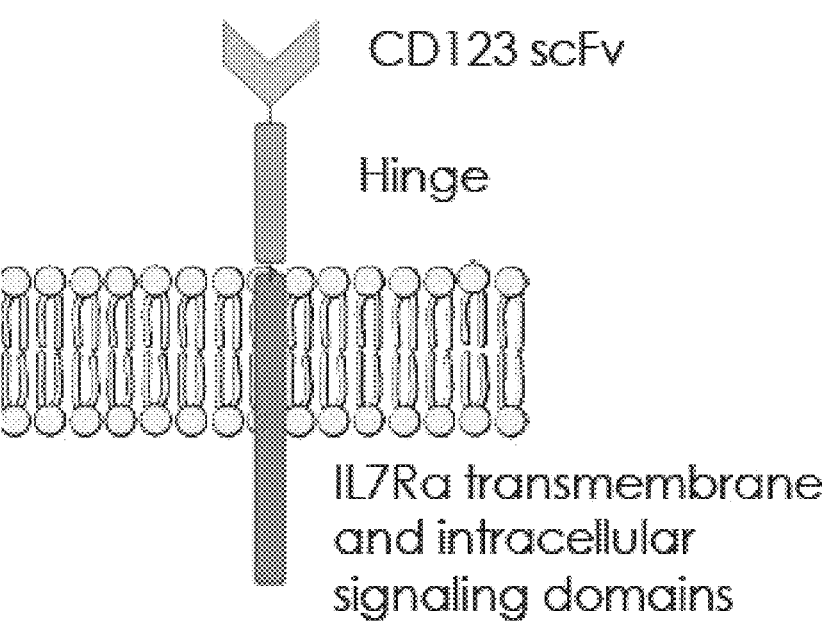
FIG. 1. Cartoon image of an exemplary CD123/IL7Ra CAR embedded in a lipid bilayer (e.g., cell membrane of an engineered T cell).

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a T cell" is a reference to one or more T cells and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "engager" ("ENG") refers to a molecule that is secreted from a cell and activates immune cells with which it interacts. The engager activates specific immune cells according to the domains present in the engager. Illustrative examples of cells that secrete engagers, but are not limited to, include T-cells, NK cells, NKT cells, CAR T-cells, mesenchymal stem cells (MSCs), neuronal stem cells, hematopoietic stem cells, antigen presenting cells (APCs), or a mixture thereof, in some cases.

As used herein, the term "bispecific" refers to any molecule or molecular complex that has two different binding specificities. The molecule or molecular complex may comprise two separate binding domains, each with the same specificity ("homobispecific") or with specificity for different molecular entities (e.g., antigens) ("heterobispecific").

As used herein, the term "antigen-recognition domain" refers to a molecular moiety (e.g. part of an engager molecule or CAR) that recognizes an antigen (e.g., antibody, antibody fragment, aptamer, receptor, cytokine, surface protein, or another antibody-based or non-antibody-based binding element). In particular embodiments, antigens can be of any nature including, but not limited to, proteins, carbohydrates, lipids, and/or synthetic molecules.

As used herein, the term "activation domain" refers to a molecular moiety (e.g. part of an engager molecule or chimeric receptor) that interacts with immune cells (e.g., T cell receptor (TCR)) and induces a positive or negative immunomodulatory signal. Illustrative examples of positive immunomodulatory signals include signals that induce cell proliferation, cytokine secretion, or cytolytic activity. Illustrative examples of negative immunomodulatory signals include signals that inhibit cell proliferation, inhibit the secretion of immunosuppressive factors, or induce cell death.

As used herein, the term "native immune cell" refers to an immune cell that naturally occurs in the immune system of a subject. Illustrative examples include, but are not limited to, T-cells, NK cells, NKT cells, B cells, and dendritic cells.

As used herein, the term "engineered immune cell" refers to an immune cell (e.g., T-cell, NK cell, NKT cell, B cell, dendritic cell, etc.) that is genetically modified.

As used herein, the term "co-stimulatory domain" or "co-stimulatory signaling domain" refers to a signaling domain of a co-stimulatory molecule. In particular aspects, it refers to a domain that provides additional signals to the immune cell in conjunction with an activation domain. Co-stimulatory molecules are cell surface molecules other than antigen receptors or Fc receptors that provide a second signal required for efficient activation and function of T lymphocytes upon binding to antigen. Illustrative examples of such co-stimulatory molecules include CD27, CD28, 4-1BB (CD137), OX40 (CD134), CD30, CD40, ICOS (CD278), LFA-1, CD2, CD7, LIGHT, NKD2C, CD70, CD80, CD86, and CD83.

The term "chimeric antigen receptor" ("CAR") refers to a recombinant polypeptide construct comprising at least an extracellular antigen-recognition domain, a transmembrane domain and an intracellular signaling domain. Upon binding to their target (e.g., displayed on a cancer cell), CARs typically modify the immune response of the immune cells they are displayed upon.

As used herein, the term "intracellular signaling domain," when used in reference to a cell surface receptor or a CAR, is a moiety responsible for activation or inhibition of at least one function of the cell upon which the receptor or CAR is displayed. The term "effector function" refers to a specialized function of a cell. For example, effector function of a T cell includes cytolytic activity or helper activity including the secretion of cytokines. Thus the term "intracellular signaling domain" refers to the portion of a protein which transduces the effector function signal and directs the cell to perform a specialized function. To the extent that a truncated portion or variant of a native intracellular signaling domain is active, such a polypeptide may be used in place of the full native chain, as long as it transduces the effector function signal. The term intracellular signaling domain includes any truncated or variant portion of a polypeptide sequence sufficient to transduce the effector function signal. Examples of intracellular signaling domains include the cytoplasmic sequences of the T cell receptor (TCR) and co-receptors that act in concert to initiate signal transduction following antigen receptor engagement, as well as any derivative or variant of these sequences and any synthetic sequence that has the same functional capability. Cytoplasmic signaling sequences that act in a stimulatory manner comprise signaling motifs which are known as immunoreceptor tyrosine-based activation motifs (ITAMs). Examples of ITAM containing cytoplasmic signaling sequences include those derived from TCR zeta, FcR gamma, FcR beta, CD3 gamma, CD3 delta, CD3 epsilon, CD3 zeta, CD5, CD22, CD79a, CD79b, and CD66d.

As used herein, the term "transmembrane domain," when used in reference to a cell surface receptor or a CAR, is a moiety that spans the plasma membrane of the cell and is connected to both the intracellular signaling domain and the extracellular antigen-recognition domain. A transmembrane domain may be derived either from a natural or from a synthetic source. Where the source is natural, the domain may be derived from any membrane-bound or transmembrane protein, for example, the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, etc. Alternatively the transmembrane domain may be synthetic, in which case it will comprise predominantly hydrophobic residues such as leucine and valine. In some embodiments, a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the intracellular signaling domain. A glycine-serine doublet provides a particularly suitable linker.

As used herein, an "immune response" refers to the action of a cell of the immune system (e.g., T lymphocytes, B lymphocytes, natural killer (NK) cells, macrophages, eosinophils, mast cells, dendritic cells, neutrophils, etc.) and soluble macromolecules produced by any of these cells or the liver (e.g., antibodies, cytokines, and complement) that results in selective targeting, binding to, damage to, destruction of, and/or elimination from a subject of invading pathogens, cells or tissues infected with pathogens, or cancerous cells or other abnormal/diseased-associated cells.

As used herein, the term "immunotherapy" refers to the treatment or prevention of a disease or condition by a method comprising inducing, enhancing, suppressing or otherwise modifying an immune response.

As used herein, the term "adoptive cell transfer" ("ACT") is the transfer of cells into a patient. The cells may have originated from the patient or from another individual or cell line.

The cells are most commonly derived from the immune system, with the goal of improving immune functionality or eliciting a desired immune response. In some embodiments, cells are extracted from a subject, genetically modified (e.g., to express a desired construct (e.g., CAR or endanger molecule)), cultured in vitro, and returned to the subject.

As used herein, the term "antibody" refers to a whole antibody molecule or a fragment thereof (e.g., fragments such as scFv, Fab, Fab', and F(ab')$_2$), unless specified otherwise; an antibody may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7$ $M^{-1}$, $>108$ $M^{-1}$, $>10^1$ $M^{-1}$, $>10^{10}$ $M^{-1}$, $>10^{11}$ $M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "antibody fragment" refers to a portion of a full-length antibody, including at least a portion antigen binding region or a variable region. Antibody fragments include, but are not limited to, Fab, Fab', F(ab')$_2$, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_{H1}$ and $C_{H2}$ domains. An interchain disulfide bond can be formed between two heavy chains of a Fab' fragment to form a "F(ab')$_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946, 778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "single-chain bispecific antibody construct" refers to a polypeptide construct comprising two antibody-derived binding domains. In some embodiments herein the two antibody-derived binding domains are an antigen-recognition domain and an activation domain. The binding domains may comprise variable regions (or parts thereof) of an antibody, antibody fragment or derivative thereof, capable of specifically binding to/interacting with a target antigen (e.g., CLL-1) or an activation molecule (e.g., human CD3 antigen). In certain embodiments, a part of a variable region comprises at least one CDR ("Complementary determining region"), such as at least a CDR1, CDR2, or CDR3 region. The two domains/regions in the single chain antibody construct are preferably covalently connected to one another as a single chain. Illustrative examples of bispecific single chain molecules are known in the art and are described in WO 99/54440; Mack, J. Immunol. (1997), 158, 3965-3970; Mack, PNAS, (1995), 92, 7021-7025; Kufer, Cancer Immunol. Immunother., (1997), 45, 193-197; Loffler, Blood, (2000), 95, 6, 2098-2103; and Bruhl, J. Immunol., (2001), 166, 2420-2426; incorporated by reference in their entireties.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin, a T-cell or B-cell receptor, or any interacting protein, such as a surface protein. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families (see above). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position. In some embodiments, peptides or polypeptides herein comprise a minimum sequence identity to a base sequence.

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

Chimeric antigen receptors (CARs) are provided that comprise a CD123-specific antigen recognition domain and IL7Ra transmembrane and intracellular signaling domains (CD123/IL7Ra CARs). In particular embodiments, provided herein are engineered lymphocytes that express and display CD123/IL7Ra CARs, and methods of targeting CD123-positive leukemic cells and treating leukemias, such as acute myeloid leukemia (AML), therewith.

Interleukin 7 (IL-7) is a human protein that is encoded by the IL7 gene. IL-7 is a hematopoietic growth factor secreted by stromal cells in the bone marrow and thymus. It is also produced by keratinocytes, dendritic cells, hepatocytes, neurons, and epithelial cells, but is not produced by normal lymphocytes. IL-7 stimulates the differentiation of multipotent (pluripotent) hematopoietic stem cells into lymphoid progenitor cells. It also stimulates proliferation of all cells in the lymphoid lineage (e.g., B cells, T cells and NK cells), and is important for proliferation during certain stages of B-cell maturation, T and NK cell survival, development and homeostasis. IL-7 is critical for T cell development and functional differentiation. IL-7 signaling occurs when IL-7 binds to the IL-7 receptor (IL7R), a heterodimer of Interleukin-7 receptor alpha (ILR7a or IL7Rα) and common gamma chain receptor. IL-7 signaling proceeds via IL7R through Jak/Stat/PI3K/Akt, and promotes T cell survival. IL7R signaling additionally potentiates T cell activation in response to low density target.

The development of engineered T cells to treat acute myeloid leukemia (AML) is has been a challenge to the field, for example, due to difficulty in target selection and the need for robust T-cell expansion and persistence. Experiments were conducted during development of embodiments herein to design a T cell stimulated to kill AML cells based on recognition of the AML-associated surface marker CLEC12A, via secretion of a CLEC12AxCD3 bispecific "engager" molecule (CLEC12A-ENG). CLEC12A-ENG T cells are specifically activated by CLEC12A, are not toxic to hematopoietic progenitor cells, and exhibit antigen-dependent AML killing. Stimulation of T-cell survival was coupled to triggering of a chimeric IL7 receptor with an ectodomain that binds a second AML-associated surface antigen, CD123. The resulting T cells, identified as CLEC12AENG.CD123IL7Rα T cells, demonstrate improved activation upon dual target recognition, kill AML, and exhibit antitumor activity in xenograft models. Enhanced T-cell activation conferred by CD123.IL7Rα was dependent both on recognition of the CD123 target and on IL7Ra-mediated downstream signaling. It is contemplated that expression of a chimeric IL7R targeted to a second tumor-associated antigen (TAA) will improve T-cell activity not only against hematological malignancies, but against other (e.g., all) cancers.

In some embodiments, IL7R-mediated T cell activation via the CARs herein (e.g., CD123/IL7Ra CARs), and engineered T cells comprising such CARs, when coupled with TCR activation (e.g., via a bispecific engager or separate CAR) provides control of full activation of engineered cells.

In some embodiments, a CD123/IL7Ra CAR comprises a CD123 scFv (or other CD123 antigen binding agent) linked to all or a portion of the transmembrane and intracellular signaling domains of IL7Ra (FIG. 5). In some embodiments, the antigen binding domain (e.g., CD123 scFv) and transmembrane domain (e.g., of IL7Ra) are attached directly. In other embodiments (e.g., as depicted in FIG. 5), the antigen binding domain (e.g., CD123 scFv) is tethered to the transmembrane domain (e.g., of IL7Ra) by a hinge domain.

In some embodiments, engineered lymphocytes are provided that display CD123/IL7Ra CARs and one or more additional cancer cell targeting elements (e.g., CARs, ENGs, etc.). In some embodiments, engineered lymphocytes express/display CD123/IL7Ra CARs and express/secrete bispecific engager molecules targeting, for example CLL. In some embodiments, engineered lymphocytes are provided comprising any suitable combination of CARs and ENGs described herein.

In some embodiments, lymphocytes are engineered to express/display chimeric antigen receptors (CARs) that bind to target cells (e.g., via an antigen-recognition domain), thereby activating the engineered T cells (e.g., via an intracellular signaling domain) against the target cells. In certain embodiments, the engineered lymphocytes display a CAR directed to CLL-1 antigen (e.g., CLL/IL7Ra CAR) and/or CD123 (e.g., CD123/IL7Ra CAR).

In some embodiments, lymphocytes are engineered to express/secrete bispecific engager molecules that bind to (i) target cells and (ii) engineered and/or native T cells, and thereby activate T cells toward the target cells. In certain embodiments, engager molecules target cells displaying a CLL-1 antigen and/or CD123 and activate T cells (e.g., engineered and/or native T cells) thereto.

In some embodiments, engineered lymphocytes expressing both a CAR and an engager molecule are provided. For example, a lymphocyte may express/display a CAR against a first antigen (e.g., CD123) and express/secrete a bispecific engager molecule against a second antigen (e.g., CLL-1) and T cell receptor (TCR). The CAR targets the engineered lymphocytes to target cells displaying the first antigen, thereby effecting an immune response by the engineered lymphocyte against the target cell, and localizing the engineered lymphocytes at a treatment site. The engager molecule binds target cells displaying the second antigen (e.g., via its antigen-recognition domain), and also binds T cells (e.g., via its activation domain), thereby effecting an immune response by the engineered lymphocytes as well as native T cells. Localization of the engineered lymphocytes by the CAR, results in release of engager molecules at the treatment cite and concentration of the immune response by the native T cells. The first and second antigens may be the same or different antigens. In some embodiments, the first and second antigens are both displayed on the surface of the target cells.

In some embodiments, CARs are provided herein that link antigen binding to IL7Ra signaling within the T cell. Such CARs turn on the T cell activation that occurs via IL-7 signaling upon binding to the extracellular target of the CAR (e.g., CD123).

Some embodiments herein relate to a strategy of adoptive cell transfer of lymphocytes transduced to express a chimeric antigen receptor (CAR), an engager molecule (ENG), or both, for the treatment of cancer (e.g., AML) or other diseases (e.g., infection) in a subject.

I. CARs

In some embodiments, provided herein are chimeric antigen receptors (CARs) and lymphocytes that are engineered to express/display a desired CAR (e.g., CD123/IL7Ra CAR). In some embodiments, T cells are engineered to express a CAR alone, engineered to express a CAR and an engager molecule, engineered to express multiple CARs, etc. In some embodiments, a cell is engineered to stably express an antibody binding domain on its surface, conferring novel antigen specificity (e.g., that is MHC independent). In some instances, a cell is engineered to express a CAR that combines an antigen recognition domain of a specific antibody with an intracellular signaling domain (e.g., IL7Ra) into a single chimeric protein.

In some embodiments, CAR cells (e.g., cells that express CAR molecules) are provided. In some embodiments, methods are provided comprising administering CAR cells to a subject provide therapy (e.g., cancer immunotherapy).

In some embodiments, a CAR comprises an extracellular domain having an antigen recognition domain, a transmembrane domain, and a cytoplasmic domain having an intracellular signaling domain. In some embodiments, a CAR further comprises a hinge domain (e.g., extracellular or intracellular hinge) or other linker between domains. In some embodiments, the transmembrane domain that naturally is associated with one of the other domains in the CAR is used. In another embodiment, the transmembrane domain is selected or modified by amino acid substitution to avoid binding of such domains to the transmembrane domains of the same or different surface membrane proteins to minimize interactions with other members of the receptor complex. In some embodiments, the transmembrane domain is the CD8 hinge domain. However, in particular embodiments herein, CARs are provided with the transmembrane domain of IL7Ra, or a fragment or variant thereof.

With respect to the cytoplasmic domain, in some embodiments a CAR comprises the CD28 and/or 4-IBB signaling domain by itself or is combined with any other desired cytoplasmic domain(s) useful in the context of the CAR. In some embodiments, the cytoplasmic domain of the CAR comprises the signaling domain of CD3-zeta. For example, the cytoplasmic domain of the CAR includes but is not limited to CD3-zeta, 4-IBB and CD28 signaling modules and combinations thereof. However, in particular embodiments herein, CARs are provided with the cytoplasmic domain (e.g., the intracellular signaling domain) of IL7Ra, or a fragment or variant thereof.

Chimeric antigen receptors provided herein comprise an extracellular and intracellular domain. The extracellular domain comprises an antigen recognition domain. In some embodiments, the intracellular domain or the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen. In other embodiments, the intracellular domain of a CAR herein comprises ro consists of all or a portion of IL7Ra, or a variant thereof.

Between the extracellular domain and the transmembrane domain of the CAR, or between the cytoplasmic domain and the transmembrane domain of the CAR, there may be incorporated a linker domain. A linker domain of a CAR is an oligo- or polypeptide that functions to link the transmembrane domain to, either the extracellular domain or, the cytoplasmic domain in the polypeptide chain. A linker domain may comprise up to 300 amino acids (e.g., 1, 2, 5, 10, 20, 30, 40, 50, 75, 100, 125, 150, 200, 250, 300, or ranges therebetween (e.g., 10 to 100 amino acids, 25 to 50 amino acids, etc.)).

In some embodiments, a CAR comprises an antigen recognition domain. The choice of antigen recognition domain depends upon the type and number of ligands that define the surface of a target cell. For example, the antigen recognition domain may be chosen to recognize a ligand that acts as a cell surface marker on target cells associated with a particular disease state. Thus, examples of cell surface markers that may act as ligands for the antigen moiety domain in the CAR of include those associated with viral, bacterial and parasitic infections, autoimmune disease and cancer cells.

In some embodiments, a CAR targets a tumor antigen of interest by displaying an antigen recognition domain that specifically binds to an antigen on a cancer cell. Cancer cell antigens are proteins that are produced by cancer cells that elicit an immune response, particularly T-cell mediated immune responses. The selection of the antigen recognition domain depends on the particular type of cancer to be treated. Cancer antigens are well known in the art. Examples of cancer antigens that may be targeted by CARs in embodiments herein include CLL-1 and CD123 antigens. In some embodiments, the cancer antigen comprises one or more antigenic cancer epitopes associated with a malignant tumor, metastatic tumor, leukemia (e.g., AML), etc.

The type of cancer antigen targeted herein (e.g., by CAR and/or by bispecific engager) may also be a cancer-specific antigen (CSA) (or tumor-specific antigen (TSA)) or a cancer-associated-antigen (CAA) (or tumor-associated-antigen (TAA)). A CSA is unique to cancer cells and does not occur on other cells in the body (e.g., healthy native cells). A CAA is not unique to a tumor cell and instead is also expressed on normal cells under conditions.

Depending on the desired antigen to be targeted, a CAR is engineered to include the appropriate antigen recognition domain that is specific to the desired antigen target. For example, in certain embodiments, if CD123 or CLL-1 is the desired antigen that is to be targeted, an antibody (or fragment thereof (e.g., scFv)) for CD123 or CLL-1 is used as the antigen recognition domain for incorporation into the CAR.

In some embodiments, the antigen recognition domain of a CAR targets CD123. In some embodiments, the antigen recognition domain in the CAR of the invention is anti-CD123 scFV.

In some embodiments, the antigen recognition domain of a CAR targets CLL-1. In some embodiments, the antigen recognition domain in the CAR of the invention is anti-CLL-1 scFV.

With respect to the transmembrane domain, in some embodiments, CARs are designed to comprise a transmembrane domain that is fused to the extracellular and intracellular domains of the CAR. In some embodiments, a transmembrane domain is a sequence that is naturally associated with one of the other domains in the CAR. In some embodiments, the transmembrane domain is selected or modified by amino acid substitution to avoid interactions with other CAR domains or cell surface components.

In some embodiments, a transmembrane domain is from either a natural or a synthetic source. Where the source is natural, the domain may be derived from any membrane-bound or transmembrane protein. Transmembrane regions of particular use include at least the transmembrane region(s) of known transmembrane proteins, including, but not limited to: the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD 154.

Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic domain of the CAR. A glycine-serine doublet provides a particularly suitable linker.

In some embodiments, the transmembrane domain of the CAR comprises a CD8 hinge domain.

In particular embodiments herein, the transmembrane domain of a CAR is all or a portion of the IL7Ra transmembrane domain, or a variant thereof.

In some embodiments, the cytoplasmic domain (a.k.a. intracellular signaling domain, activation domain, etc.) of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While the entire intracellular signaling domain of a known protein or protein complex may be employed in certain embodiments, in other embodiments it is not necessary to use the entire chain. To the extent that a truncated portion of a known intracellular signaling domain is used, such truncated portion may be used in place of the intact chain as long as it transduces the effector function signal. Examples of intracellular signaling domains for use in the CARs herein include the cytoplasmic sequences of the T cell receptor (TCR) and co-receptors that act in concert to initiate signal transduction following antigen-receptor engagement, as well as any derivative or variant of these sequences and any synthetic sequence that has the same functional capability. In particular embodiments herein, the intracellular signaling domain of a CAR is all or a portion of the IL7Ra intracellular signaling domain, or a variant thereof.

In some embodiments, signals generated through the TCR alone are insufficient for full activation of the T cell; a secondary or co-stimulatory signal is also required for full activation. Thus, in some embodiments, T cell activation is mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences). Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of 1TAM containing primary cytoplasmic signaling sequences that are of particular use in the invention include those derived from TCR zeta, FcR gamma, FcR beta, CD3 gamma, CD3 delta, CD3 epsilon, CDS, CD22, CD79a, CD79b, and CD66d. In some embodiments, a cytoplasmic signaling molecule in the CAR of the invention comprises a cytoplasmic signaling sequence derived from CD3 zeta.

In some embodiments, the cytoplasmic domain of the CAR comprises a primary signaling sequence (e.g., CD3-zeta signaling domain) by itself or combined with any other desired cytoplasmic domain(s) useful in the context of the CAR. For example, the cytoplasmic domain of the CAR may comprise a primary signaling sequence and a costimulatory signaling region. The costimuiatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-I BB (CD 137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like.

The cytoplasmic signaling sequences within the cytoplasmic signaling portion of the CAR may be linked to each other in a random or specified order. Optionally, a short oligopeptide linker (e.g., between 2 and 25 amino acids in length) forms the linkage. A glycine-serine doublet provides a particularly suitable linker.

In particular embodiments, the cytoplasmic signaling portion of a CAR herein comprises all or a portion of the IL7Ra intracellular signaling domain, or a variant thereof.

While a variety of CARs comprising various combinations of antigen binding domains, transmembrane domains, and intracellular signaling domains are encompassed by embodiments herein, particular embodiments herein comprise CARs having: (a) an antigen binding domain that recognizes (binds to) an epitope on CD123 (e.g., an anti-CD123 antibody or fragment thereof (e.g., anti-CD123 scFv)), (b) a transmembrane domain comprising all or a portion of the transmembrane domain of IL7Ra (or a variant thereof); and an intracellular signaling domain comprising all or a portion of the intracellular signaling domain of IL7Ra (or a variant thereof).

In some embodiments, a CAR binds to CD123 (e.g., one or more epitopes on CD123) and induces IL-7 signaling (IL7Ra signaling) within a T cell. In some embodiments, CD123 binding a CAR on an engineered T cell induces signaling via Jak/Stat/PI3K/Akt.

In some embodiments, a CAR comprises an antigen binding domain that recognizes (binds to) CD123 and/or an epitope on CD123. In some embodiments, all or a portion of the antigen binding domain comprises 70% or greater (e.g., 70%, 75%, 80%, 85%, 90%, 95%, 100%, or ranges therebetween) sequence identity with SEQ ID NO: 6 or a portion thereof (e.g., a portion 25 amino acids in length or greater (e.g., 25 amino acids, 50 amino acids, 75 amino acids, 100 amino acids, or more, or ranges therebetween).

In some embodiments, a CAR comprises a IL7Ra transmembrane domain. In some embodiments, all or a portion of the IL7Ra transmembrane domain comprises 70% or greater (e.g., 70%, 75%, 80%, 85%, 90%, 95%, 100%, or ranges therebetween) sequence identity with SEQ ID NO: 2 or a portion thereof (e.g., a portion 25 amino acids in length or greater (e.g., 25 amino acids, 50 amino acids, 75 amino acids, 100 amino acids, or more, or ranges therebetween). In some embodiments, all or a portion of the IL7Ra transmembrane domain comprises 70% or greater (e.g., 70%, 75%, 80%, 85%, 90%, 95%, 100%, or ranges therebetween) sequence identity with SEQ ID NO: 3 or a portion thereof (e.g., a portion 25 amino acids in length or greater (e.g., 25 amino acids, 50 amino acids, 75 amino acids, 100 amino acids, or more, or ranges therebetween).

In some embodiments, a CAR comprises a IL7Ra intracellular signaling domain. In some embodiments, all or a portion of the IL7Ra intracellular signaling comprises 70% or greater (e.g., 70%, 75%, 80%, 85%, 90%, 95%, 100%, or ranges therebetween) sequence identity with SEQ ID NO: 4 or a portion thereof (e.g., a portion 25 amino acids in length or greater (e.g., 25 amino acids, 50 amino acids, 75 amino acids, 100 amino acids, or more, or ranges therebetween).

In some embodiments, a CAR comprises a hinge domain comprising 70% or greater (e.g., 70%, 75%, 80%, 85%, 90%, 95%, 100%, or ranges therebetween) sequence identity with SEQ ID NO: 5 or a portion thereof (e.g., a portion 25 amino acids in length or greater (e.g., 25 amino acids, 50 amino acids, 75 amino acids, 100 amino acids, or more, or ranges therebetween).

II. Engager Molecules

In some embodiments, provided herein are compositions comprising engager molecules (e.g., a bispecific engager molecule), wherein the engager molecule comprises (i) a domain that binds to an antigen on an immune cell surface (e.g., native or engineered immune cell surface) and (ii) an domain that binds to a target cell antigen (e.g., an antigen expressed on the surface of tumor cell, cancer cell, or other disease-related cell).

In some embodiments, engager cells (e.g., cells that express and bispecific engager molecules) are provided. In some embodiments, methods are provided comprising administering engager cells to a subject provide therapy (e.g., cancer immunotherapy).

In some embodiments, cells (e.g., immune cells) are genetically modified to express engager molecules comprising at least (i) an antigen-recognition domain and (ii) an activation domain. In some embodiments, engager molecules expressed by engineered cells further comprise one or more accessory domains, such as a cytokine domain, costimulatory domain, a domain for inhibition of negative regulatory molecules of T-cell activation, etc. In some embodiments, an antigen-recognition domain, an activation domain, and/or any accessory domains present in an engager molecule are directly linked or are linked by a linker domain. In some embodiments the linker domain has contained within it a functional moiety, for example, the activation domain of a human cytokine.

In some embodiments, the antigen-recognition domain of an engager molecule binds to one or more molecules present in and/or on target cells or that are secreted by target cells. In particular embodiments, target cells are cancer cells, including at least hematological tumor cells (e.g., hematological malignancies derived from myeloid cell lines). Engager molecules bound to an antigen on a target molecule, are capable of activating immune cells (e.g., engineered or native immune cells) that express/display the molecular determinant recognized by the activation domain of the engager molecule. Engager molecules activate engineered immune cells (e.g., those expressing/secreting engager molecules, those engineered to express other immunotherapeutically-useful agents, etc.) that express/display the molecular determinant recognized by the activation domain. Engager molecules also activate native immune cells (e.g., unmodified immune cells that are native to the subject being treated) that express/display the molecular determinant recognized by the activation domain. Immune cell activation results in a positive or negative signal, depending upon the molecular determinant recognized by the activation domain. Examples of positive signals include signals that induce cell proliferation, cytokine secretion, or cytolytic activity. Examples of negative signals include signals that inhibit-cell proliferation, inhibit the secretion of immunosuppressive factors, or induce cell death. By activating native immune cells, engineered immune cells that secrete engager molecules redirect resident (e.g., naturally endogenous to a specific individual) immune cells to target cells.

In some embodiments, engager molecules comprise a polypeptide chain comprising an antigen-recognition domain and an activation domain. In some embodiments, the antigen-recognition domain and the activation domain are linked directly. In other embodiments, the antigen-recognition domain and the activation domain are connected by a linker peptide. In some embodiments, an engager molecule is a single-chain bispecific antibody construct. In some embodiments, the antigen-recognition domain is a single chain variable fragment that binds a target cell antigen. In some embodiments, the activation domain is a single chain variable fragment that engages the TCR. In some embodiments, both the activation domain and the antigen-recognition domain are scFv's and the individual moieties are arranged and oriented in any suitable manner, for example:

$$N-V_{H-AD}-L_1-V_{L-AD}-L_2-V_{H-ARD}-L_3-V_{L-ARD}-C;$$

$$N-V_{L-AD}-L_1-V_{H-AD}-L_2-V_{H-ARD}-L_3-V_{L-ARD}-C;$$

$$N-V_{H-AD}-L_1-V_{L-AD}-L_2-V_{L-ARD}-L_3-V_{H-ARD}-C;$$

$$N-V_{L-AD}-L_1-V_{H-AD}-L_2-V_{L-ARD}-L_3-V_{H-ARD}-C;$$

$$N-V_{H-ARD}-L_1-V_{L-ARD}-L_2-V_{H-AD}-L_3-V_{L-AD}-C;$$

$$N-V_{L-ARD}-L_1-V_{H-ARD}-L_2-V_{H-AD}-L_3-V_{L-AD}-C;$$

$$N-V_{H-ARD}-L_1-V_{L-ARD}-L_2-V_{L-AD}-L_3-V_{H-AD}-C;$$

$$N-V_{L-ARD}-L_1-V_{H-ARD}-L_2-V_{L-AD}-L_3-V_{H-AD}-C;$$

wherein N- is the N-terminus; $V_H$ is the heavy chain variable region; $V_L$ is the light chain variable region; $L_1$, $L_2$, and $L_3$ are linker peptides; -C is the C-terminus; ARD is antigen-recognition domain; and AD is activation domain. In some embodiments, $L_1$ and $L_3$ are of appropriate length and sequence to allow the activation scFv and the antigen-binding scFv to each function properly (e.g., bind to TCR and antigen, respectively) individually, and $L_2$ is or proper length and sequence to allow the activation scFv and antigen-binding scFv to both function (e.g., bind to TCR and antigen) within a single bispecific construct (e.g., engager molecule). In some embodiments, $L_1$, $L_2$, and/or $L_3$ may be absent from the above constructs.

In some embodiments, an engager molecule comprises an antigen recognition domain. The choice of antigen recognition domain depends upon the type and number of ligands that define the surface of a target cell. For example, the antigen recognition domain may be chosen to recognize a ligand that acts as a cell surface marker on target cells associated with a particular disease state. Thus, examples of cell surface markers that may act as ligands for the antigen recognition (or binding) domain in the engager molecule include those associated with viral, bacterial and parasitic infections, autoimmune disease and cancer cells. In some embodiments, an engager molecule comprises an antigen-recognition domain that binds to an antigen presented on the surface of a diseased cell or cell that is the source of disease. In particular embodiments, the antigen-recognition domain binds to an antigen presented on a cancer cell or a tumor cell. Any cancer antigen may be targeted by the engager-expressing T-cells or the corresponding engager molecules thereof. In some embodiments, the antigen-recognition domain binds to an antigen presented on cells of hematopoietic and lymphoid malignancies. In some embodiments, the antigen-recognition domain binds to an antigen presented on cells of myeloid malignancies. In some embodiments, the antigen-recognition domain binds to an antigen presented on cells of acute and chronic myelogenous leukemia, myelodysplastic syndromes and myeloproliferative diseases. In certain embodiments, the antigen-recognition domain binds to an antigen presented on cells of myeloid malignancies but not myeloid progenitor cells. In particular embodiments, the antigen-recognition domain binds to C-type lectin domain family 12 member A; a human protein which is encoded by the CLL-1 gene; is also referred to as CLEC12A, CLL1, DCAL-2, MICL, and CD371; and is typically referred to herein as CLL-1. Experiments conducted during development of embodiments herein demonstrate the utility advantageousness of engager molecules comprising CLL-1 antigen-recognition domains and lymphocytes expressing/secreting such engager molecules; however, embodiments herein are not limited to CLL-1 antigen-recognition domains.

In some embodiments, a bispecific engager targets a tumor antigen of interest by displaying an antigen recognition domain that specifically binds to an antigen on a cancer cell. Cancer cell antigens are proteins that are produced by cancer cells that elicit an immune response, particularly T-cell mediated immune responses. The selection of the antigen recognition domain depends on the particular type of cancer to be treated. Cancer antigens are well known in the art. Examples of cancer antigens that may be targeted by bispecific engagers in embodiments herein include CLL-1 and CD123 antigens. In some embodiments, the cancer antigen comprises one or more antigenic cancer epitopes associated with a malignant tumor, metastatic tumor, leukemia (e.g., AML), etc.

The type of cancer antigen targeted herein (e.g., by a bispecific engager) may also be a cancer-specific antigen (CSA) (or tumor-specific antigen (TSA)) or a cancer-associated-antigen (CAA) (or tumor-associated-antigen (TAA)). A CSA is unique to cancer cells and does not occur on other cells in the body (e.g., healthy native cells). A CAA is not unique to a tumor cell and instead is also expressed on normal cells under conditions.

Depending on the desired antigen to be targeted, a bispecific engager is engineered to include the appropriate antigen recognition domain that is specific to the desired antigen target. For example, in certain embodiments, if CD123 or CLL-1 is the desired antigen that is to be targeted, an antibody (or fragment thereof (e.g., scFv)) for CD123 or CLL-1 is used as the antigen recognition domain for incorporation into the bispecific engager.

In some embodiments, an engager molecule comprises an activation domain that allows the engager molecule to bind to an immunoresponsive cell (e.g., T cell). In some embodiments, the activation domain binds to a surface displayed ligand, antigen, receptor, etc. on the engineered lymphocyte from which it was expressed. In some embodiments, the activation domain binds to a surface displayed ligand, antigen, receptor, etc. on native lymphocytes. In some embodiments, the activation domain binds to native lymphocytes but not engineered lymphocytes. In some embodiments, the activation domain binds to native lymphocytes and engineered lymphocytes. In some embodiments, the activation domain is an antibody or antigen-binding fragment thereof (e.g., scFv). Illustrative examples of activation domains include, but are not limited to antibodies, antigen-binding antibody fragments, ligands, peptides, soluble T-cell receptors, or combinations thereof.

The immune cell to which the engager binds may be an unmodified naturally endogenous (to the recipient individual) immune cell (e.g., native lymphocyte), or it may be a genetically modified immune cell (e.g., engineered lymphocyte). Binding of the engager to the target immune cell (e.g., to the TCR) through the activation domain (e.g., via a CD3 antibody of antibody fragment), thereby activates the target immune cell. When the engager is to target NK cells, the activation domain may comprise of an antibody that recognizes, for example, CD16 (such as NM3E2 antibody), or ligands specific for NKG2D (ULBP2), or NKp30 (B7H6). In specific embodiments, the activation domain comprises ligands, receptors, peptides, etc.

In some embodiments, an engager molecule comprises an activation domain that targets co-stimulatory molecules such as CD27, CD28, CD134, and CD137. In some embodiments, such engager molecules are used in concert with other engager molecules (e.g., engager molecule with activation domains that directly stimulate lymphocytes (e.g., that bind the TCR). For example, T-cells are engineered to express a first engager molecule with a CLL-1-specific antigen recognition domain and a CD3-specific activation domain, and another engager with a CD123-specific antigen recognition domain and a CD28-specific activation domain. T-cells would only be fully activated (e.g., activated by both CD3 and CD28 binding) at tumor sites at which both CLL-1 and CD123 antigens are expressed. In some embodiments, co-stimulatory engager molecules are used in concert with engineered lymphocytes that express/display chimeric antigen receptors. For example, T-cells are engineered to express a chimeric antigen receptor with an CD123-specific antigen recognition domain, and an engager molecule with a CLL-1-specific antigen recognition domain and a CD28-specific activation domain. These engineered T-cells would target any cells displaying a CD123 antigen, but would only be fully activated (at tumor sites at which both CLL-1 and CD123 antigens are expressed. Other combinations of primary (e.g., CD3, TCR, etc.) and co-stimulatory activation domains with engagers, CARs, etc. are within the scope herein.

In some embodiments, in addition to activation, linker, and antigen-recognition domains, an engager molecule comprises one or more additional functional domains (and optionally additional linker domains). Such engager molecules may be trispecific (e.g., capable of binding to three ligands) or multispecifc (e.g., capable of binding to two or more (e.g., 2, 3, 4, 5, 6, 7, 8, or more) ligands) or may be bispecific but further comprise additional functionality (e.g., targeting peptide, therapeutic peptide, luminescence, fluorescence, etc.).

Additional functional domains may comprise a cytokine, costimulatory domain, and/or domain for inhibition of negative regulatory molecules of T-cell activation.

As addressed above, in some embodiments, engager molecules comprise one or more linker domains (e.g., between heavy and light variable chains, between activation and antigen-recognition domains, etc.). Linkers that facilitate the formation and activity of scFv constructs (e.g., $L_1$- and $L_3$-type linkers, linkers between heavy and light variable chains) are well understood in the art. In some embodiments, such linkers are about 5 to 50 amino acids in length (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or ranges therebetween (e.g., 10-25)). In some embodiments, linkers are glycine rich (e.g., >20%, >30%, >40%, >50%) to impart flexibility to the linker. In some embodiments, linkers are serine and/or threonine rich (e.g., >20%, >30%, >40%, >50%) to impart solubility to the linker. In some embodiments, linkers are of any suitable length and sequence so as to allow the formation of active activation and antigen-recognition domains. In some embodiments, linkers between the activation and antigen-recognition domains (e.g., $L_2$-type linkers) comprise similar characteristics (e.g., to $L_1$- and $L_3$-type linkers). In some embodiments, linkers between the activation and antigen-recognition domains (e.g., $L_2$-type linkers) are of any suitable length and sequence so as to allow the formation of active activation and antigen-recognition domains, without adverse interaction occurring between the domains.

III. Cells and Nucleic Acids

In some embodiments, provided herein are lymphocytes engineered to express one or more chimeric antigen receptors (CARs) and/or engager molecules (e.g., those described above). Engineered cells may be generated by any suitable method in the art. In specific embodiments, the engineered lymphocytes are generated by viral transduction of lymphocytes, (e.g., T-cell, NK cell, NKT cell, B cell, dendritic cell, etc.). In some embodiments, lymphocytes are engineered to express/display one or more CARs (e.g., targeting CD123 (e.g., CD123/IL7Ra), CLL-1 (e.g., (e.g., CLL/IL7Ra), etc.), and/or other antigens). In some embodiments, lymphocytes are engineered to express/secrete one or more engager molecules (e.g., targeting CD123, CLL-1, and/or other antigens). In some embodiments, lymphocytes are engineered to express/display one or more CARs (e.g., targeting CD123 (e.g., CD123/IL7Ra), CLL-1 (e.g., (e.g., CD123/IL7Ra), and/or other antigens) and to express/secrete one or more engager molecules (e.g., targeting CD123, CLL-1, and/or other antigens).

Provided herein are nucleic acids and nucleic acid sequences encoding CARs and bispecific engager molecules as described above and cells harboring such nucleic acids. In some embodiments, nucleic acid molecules are recombinant nucleic acid molecules. In some embodiments, nucleic acid molecules are synthetic. Nucleic acids encoding bispecific engager molecules and/or CARs may comprise DNA, RNA, PNA (peptide nucleic acid), and hybrids thereof.

In some embodiments, a nucleic acid encoding a bispecific engager molecule and/or CAR comprises one or more regulatory sequences. For example, promoters, transcriptional enhancers and/or sequences that allow for induced expression of the polynucleotide of the disclosure may be employed. In some embodiments, nucleic acid molecules are transcribed by an appropriate vector comprising a chimeric gene that allows for the transcription of the nucleic acid molecule in the cell.

In some embodiments, a nucleic acid molecule is a recombinantly-produced chimeric nucleic acid molecule comprising any of the aforementioned nucleic acid molecules either alone or in combination. In some embodiments, the nucleic acid molecule is part of a vector.

In some embodiments, provided herein are vectors comprising the nucleic acid molecule described herein (e.g., encoding CARs and/or engager molecules). Many suitable vectors are known to those skilled in molecular biology, the choice of which would depend on the function desired and include plasmids, cosmids, viruses, bacteriophages and other vectors used conventionally in genetic engineering. Methods that are well known to those skilled in the art can be used to construct various plasmids and vectors; see, for example, the techniques described in Sambrook et al. (1989) and Ausubel, Current Protocols in Molecular Biology, Green Publishing Associates and Wiley Interscience, N.Y. (1989), (1994); incorporated by reference in its entirety. Alternatively, the polynucleotides and vectors of the disclosure are reconstituted into liposomes for delivery to target cells. A cloning vector may be used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

In some embodiments, a vector comprises a nucleic acid sequence that is a regulatory sequence operably linked to the nucleic acid sequence encoding a CAR and/or engager molecule described herein. Such regulatory sequences (control elements) are known to the artisan and may include a promoter, a splice cassette, translation initiation codon, and insertion site for introducing an insert into the vector. In specific embodiments, the nucleic acid molecule is operatively linked to said expression control sequences allowing expression in eukaryotic or prokaryotic cells.

In some embodiments, the vector is a viral vector, such as a lentiviral vector or adenovirus associate vector.

In some embodiments, nucleic acids and/or vectors are used in a cell to express encoded polypeptides (e.g., CARS, engager molecules, etc.) in the cells. The nucleic acid molecules or vectors containing the DNA sequence(s) encoding any of the CAR and/or engager constructs herein are introduced into the cells that in turn produce the polypeptide(s). The recited nucleic acid molecules and vectors may be designed for direct introduction or for introduction via liposomes, or viral vectors (e.g., adenoviral, retroviral) into a cell. In certain embodiments, the cells are T-cells, CAR T-cells, NK cells, NKT-cells, MSCs, etc.

In accordance with the above, provided herein are methods to derive vectors, particularly plasmids, cosmids, viruses and bacteriophages used conventionally in genetic engineering that comprise a nucleic acid molecule encoding a polypeptide sequence (e.g., a CAR and/or engager) described herein. In some embodiments, a vector is an expression vector and/or a gene transfer or targeting vector. Expression vectors derived from viruses such as retroviruses, vaccinia virus, adeno-associated virus, herpes viruses, or bovine papilloma virus, may be used for delivery of polynucleotides and/or vectors into targeted cell populations. Methods which are well known to those skilled in the art can be used to construct recombinant vectors. Vectors are transferred into the host cells by well-known methods, which vary depending on the type of cellular host.

In some embodiments, provided herein are cells comprising a host cell transformed or transfected with a vector defined herein above (e.g., encoding a engager or CAR described herein). The host cell may be produced by introducing at least one of the above described vectors or at least one of the above described nucleic acid molecules into the host cell. The presence of the at least one vector or at least one nucleic acid molecule in the host may mediate the expression of a gene encoding the above described CAR and/or engager. The nucleic acid molecule or vector that is introduced in the host cell may either integrate into the genome of the host or it may be maintained extrachromosomally.

In some embodiments, provided herein are methods comprising culturing a host cell defined herein above under conditions allowing the introduction of the nucleic acid and/or vector. In some embodiments, provided herein are methods comprising culturing a host cell defined herein above under conditions allowing expression of a construct (e.g., comprising a CAR and/or engager). In particular embodiments, the cultured cells (e.g., expressing/displaying a CAR and/or expressing/secreting an engager molecule) are provided to a subject (e.g., from which the original cells were obtained, a second subject, etc.). Conditions for the culturing of cells harboring an expression construct are known in the art.

In some embodiments, nucleic acids encoding the polypeptides (e.g., CARs, engager molecules, etc.) are inserted into the genetic material of a host cell (parent cell) using a CRISPR/Cas9 system. CRISPRs are DNA loci comprising short repetitions of base sequences. Each repetition is followed by short segments of "spacer DNA" from previous exposures to a virus. CRISPRs are often associated with Cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. The CRISPR/Cas system may be used for gene editing. By delivering the Cas9 protein and appropriate guide RNAs into a cell, the organism's genome can be cut at any desired location. Methods for using CRISPR/Cas9 systems, and other systems, for insertion of a gene into a host cell to produce an engineered cell are described in, for example, U.S. Pub. No. 20180049412; herein incorporated by reference in its entirety.

In some embodiments, lymphocytes for engineering according to embodiments herein are from any suitable source. For example, a source of lymphocytes is a subject (e.g., the subject to be treated, a healthy subject, etc.). Lymphocytes can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, a specific type of lymphocyte (e.g., T cell, NK cell, B cell, etc.) desired for an embodiment described herein is obtained by appropriate methods. In some embodiments, lymphocytes expressing a particular marker are obtained by known methods (e.g., cell sorting). In some embodiments, cells are cultured following isolation. In some embodiments, cells are engineered using methods described herein.

IV. Treatments and Therapeutics

In various embodiments herein, CARs, engager molecules, nucleic acid sequences, vectors, host cells, engineered lymphocytes, etc. as contemplated herein and/or pharmaceutical compositions comprising the same are used for the prevention, treatment or amelioration of a cancerous disease, such as, for example AML.

In some embodiments, compositions herein (e.g., CAR-cells, ENG-cells, nucleic acid molecules and vectors, engineered lymphocytes, etc.) are administered either alone or in any combination using standard delivery systems and methods, and in at least some aspects, together with a pharmaceutically acceptable carrier or excipient. In the case of nucleic acid molecules or vectors, they may be stably integrated into the genome of the subject.

In some embodiments, methods and compositions are provided relating to the prevention, treatment or amelioration of a cancer comprising the step of administering to a subject in the need thereof an effective amount of cells harboring a CAR, an engager molecule, a nucleic acid sequence, a vector, as contemplated herein and/or produced by a process as contemplated herein. When cells are administered, the engineered cells are either administered to a site of treatment or may localize at a site of treatment (e.g., cell type, tissue type, etc.).

In some embodiments, indications for administration of the composition(s) herein are cancerous diseases. Examples of hematological (or hematogenous) cancers that are treated/prevented in embodiments herein include leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myeiodysplastic syndrome, hairy cell leukemia and myelodysplasia. Examples of solid tumors that are treated/prevented in embodiments herein include, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous eel! carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medu!loblastoma, Schwannoma craniopharyogioma, ependymoma, pineaioma, hemangioblastoma, acoustic neuroma, oligodendroglioma, menangioma, neuroblastoma, retinoblastoma and brain metastases).

The disclosure further encompasses co-administration protocols with other compounds, e.g., bispecific antibody constructs, targeted toxins or other blocking or functional antibodies or compounds, which act via immune cells. The clinical regimen for co-administration may encompass co-administration at the same time, before or after the administration of the other component. Particular combination therapies include chemotherapy, radiation, surgery, hormone therapy, or other types of immunotherapy. Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In some embodiments, the engineered lymphocytes or other compositions described herein are co-administered with one or more chemotherapeutics. Chemotherapies for use with the engineered lymphocytes described herein include all classes of chemotherapeutic agents, such as, alkylating agents, antimetabalites, plant alkaloids, antibiotics, hormonal agents, and miscellaneous anticancer drugs. Specific agents include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, fuldarabine, navelbine, farnesyl-protein tansferase inhibitors, transplatinum, 5-fluorouracil, vincristin, and vinblastin, or any analog or derivative variant of the foregoing and also combinations thereof. In some embodiments, chemotherapy is employed before, during and/or after administration of engineered lymphocytes or other compositions described herein.

In some embodiments, the engineered lymphocytes or other compositions described herein are co-administered with radiotherapy, methods of which are understood in the field. In some embodiments, radiotherapy is employed before, during and/or after administration of or other compositions described herein.

In some embodiments, the engineered lymphocytes or other compositions described herein are co-administered with non-immune based targeted therapies, such as, agents that inhibit signaling pathways such WNT, p53, and/or RB-signaling pathways. Other examples include agents that inhibit tyrosine kinases, BRAF, STAT3, c-met, regulate gene expression, induce cell death or block blood vessel formation. Examples of specific agents include imatinib mesylate, dasatinib, nilotinib, bosutinib, lapatinib, gefinitib, erlotinib, tensirolimus, everolimus, vemurafenib, crizotinib, vorinostat, romidepsin, bexarotene, alitrionin, tretionin, bortezomib, carfilzomib, pralatrexate, sorafenib, sunitinib, pazopanib, regorafenib, or cabozantinib. In some embodiments, non-immune based targeted therapy is employed before, during and/or after administration of or other compositions described herein.

In some embodiments, the engineered lymphocytes or other compositions described herein are co-administered with an immunotherapy. Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect-cell killing. The antibody may also prevent cancer immunoevasion or immunosuppression. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T-cells, NKT cells, and NK cells. In some embodiments, immunotherapy is employed before, during and/or after administration of or other compositions described herein. In some embodiments, engineered lymphocytes are co-administered with an immune checkpoint inhibitor (e.g., anti-PD1, anti-PDL1, anti-CTLA-4, etc.).

In some embodiments, the engineered lymphocytes or other compositions described herein are co-administered with a gene therapy in which a therapeutic polynucleotide is administered before, after, or at the same time as the engineered lymphocytes described herein. A variety of expression products are encompassed, including inducers of cellular proliferation, inhibitors of cellular proliferation, or regulators of programmed cell death.

In some embodiments, the engineered lymphocytes or other compositions described herein are administered before, during, and/or after surgery. Surgeries include resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that embodiments herein may be used in conjunction with removal of superficial cancers, precancers, or incidental amounts of normal tissue.

In some embodiments, the engineered lymphocytes or other compositions described herein are co-administered with other agents to improve the therapeutic efficacy of treatment.

In some embodiments, engineered lymphocytes or other compositions described herein are provided as part of a kit or system along with one or more additional components, such as instructions, devices for administration, additional therapeutic agents, diagnostic agents, research agents, etc.

EXPERIMENTAL

Example 1

Immune Stimulation

Figure 2:
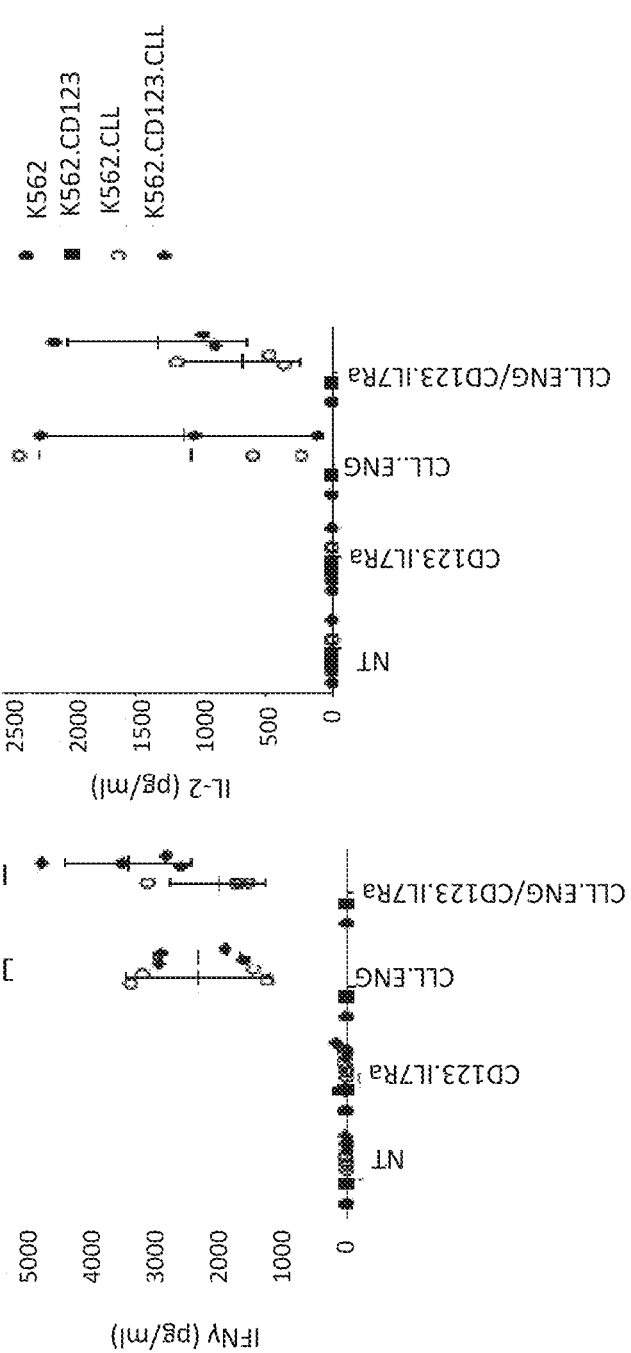
FIG. 2. Graphs depicting IFN and IL-2 cytokine induction by T cells expressing CD123/IL7Ra CARs, CLL/CD3 ENG, both, or neither in the presence of K562 cells displaying CD123, CLL, both, or neither.

Experiments were conducted during development of embodiments herein to demonstrate to compare the immune response activation by T cells expressing CD123/IL7Ra CARs, CLL/CD3 bispecific engagers, neither or both, in the presence of K562 myelogenous leukemia cells expressing CD123, CLL, both or neither (FIG. 2). The CD123/IL7Ra CAR T cells did not produce cytokine under any condition. CLL-ENG T cells were activated in the presence of target CLL. CD123 alone did not activate CLL-ENG. However, the T cells expressing both the CD123.IL7a CAR and secreting CLL-ENG molecules exhibited enhanced stimulation of immune response, as measured by IFN and IL-2 concentration, when challenged with K562 cells displaying both CLL and CD123. These results indicate that the combination of the IL7Ra-linked CAR and bispecific engager is effective in maximizing specific response to populations of leukemia cells.

Cytoxicity

Experiments were conducted during development of embodiments herein to demonstrate cytoxicity of T cells expressing CD123/IL7Ra CARs, CLL/CD3 ENG, both, both bicistronically, or neither in the presence of K562 cells displaying CD123, CLL, both, or neither (FIG. 3). T cells expressing both CD123/IL7Ra CARs and CLL/CD3 ENGs (bicistronically or on separate vectors) exhibit similar cytoxicity to T Cells expressing CLL/CD3 ENG alone.

In Vivo

Experiments were conducted in mice during development of embodiments herein to demonstrate the persistence of T cells expressing the CD123/IL7Ra CAR (FIG. 4). Mice were injected with leukemia engineered for stable expression of firefly luciferase (ffLuc) on Day 0. The ffLuc enables non-invasive monitoring of leukemia burden serially in mice. This is achieved via injection of the metabolite D-Luciferin that is metabolized by ffLuc to cause emission of bioluminescence (BLI). Mice were administered T cells on day 7. The top panel of FIG. 3 represents BLI emitted by mice, which is a reprentation of leukemia burden over time. Mice treated with unmodified T cells show no impact on leukemia proliferation following T cell injection. In contrast, mice receiving CLL-ENG or CLL-ENG.I.CD123IL7Ra expressing T cells demonstrate anti-leukemia effect of administered cells. In addition to BLI monitoring, peripheral blood was drawn at day 42 and day 56 and evaluated using flow cytometry. Antibodies to human CD45 and human CD3 were used to enable quantification of human T cells (hCD45 and hCD3+) per microliter of blood. Results demonstrate increased percentage of T cells in CD123/IL7Ra CAR group, indicating CD123.IL7Ra promotion of T cell survival.

Example 2

Materials and Methods

Cells and Culture Conditions.

293T, MV-4-11, OCI-AML-3, and K562 cell lines were purchased from the American Type Culture Collection (ATCC, Manassas, VA) and cultured in Dulbecco's Modified Eagle Medium (DMEM, ThermoFisher Scientific, Waltham, MA; 293T, MV-4-11), Roswell Park Memorial Institute (RPMI, ThermoScientific; OCI-AML-3), or Iscove's Modified Dulbecco's Medium (IMDM, ThermoFisher; K562) supplemented with 10% Fetal Bovine Serum (FBS, ThermoScientific). All cells were maintained in a humidified atmosphere containing 5% $CO_2$ at 37° C. K562 cells expressing CD123 (K562.CD123), CLEC12A (K562.CLEC12A), or CD123 and CLEC12A (K562.CD123.CLEC12A) were generated by first subcloning the full length human CD123 (NCBI Accession: NP_002174.1) or CLEC12A coding sequence (NCBI Accession: NP_612210.4) into a pCDH lentiviral backbone (System Biosciences, Inc., Mountain View, CA). VSVG-pseudotyped lentiviral particles were produced according to the manufacturer's instructions. K562 cells were then transduced with the virus and antigen expression verified with flow cytometric analyses. Cells were isolated via fluorescence-activated cell sorting (FACS) and expression verified prior to use. All cells used for cytotoxicity analysis were generated by transducing the cell line with a retroviral vector encoding an enhanced GFP firefly luciferase fusion gene (GFP.ffLuc) (Ref. 14: herein incorporated by reference in its entirety). GFP-positive cells were sorted and maintained in the appropriate culture medium. Luciferase expression was confirmed using Dluciferin and quantification of bioluminescence. The identity of all progeny of cell lines generated and used in this study were authenticated using American Type Culture Collection (ATCC, Manassas, VA) human STR profiling cell authentication service. MV4-11, MV-4-11.ffLuc in 2016 were authenticated in 2016. OCI-AML-3 were not authenticated, though the progeny OCI-AML-3.ffLuc were, in 2016. K562 cells were authenticated in 2016 and K562.ffLuc in 2017. Following authentication, cells were stored in a cell bank and freshly thawed for each set of experiments. Cells were not kept in culture for longer than one month. Mycoplasma testing was routinely performed and was not found positive in any cell line used for generation of data in this manuscript at any time.

Construction of Viral Vectors

Figure 5A:
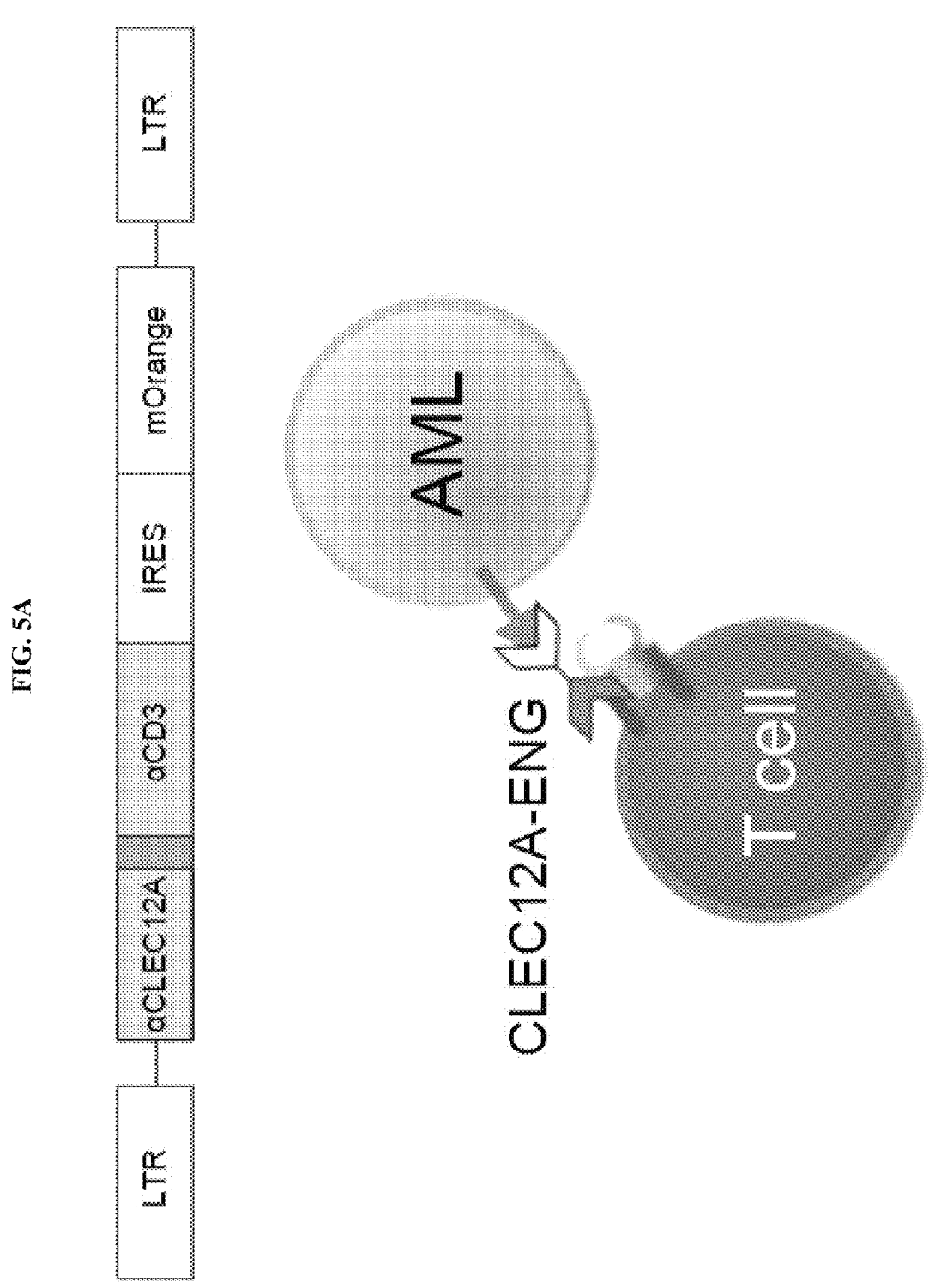
FIGS. 5A-D. CLEC12A-targeting with CLEC12A-ENG T cells has specific anti-leukemic activity in vitro. A. Schematic of construct used for targeting and method of T-cell activation. B. Transduction efficiency of CLEC12A-ENG T cells. (n=10-12 independent T-cell donors). C. Interferon-γ secreted by CLEC12A-ENG T cells after overnight culture with CLEC12A− (K562) or CLEC12A+ (MV-4-11, OCI-AML-3) AML cell lines. Unmodified (NT) and CD19-specific T cells (CD19-ENG) included as controls. (n=4-6 independent donors, difference noted between CLEC12A-ENG and NT T cells. D. CLEC12A+ (MV-4-11, OCI-AML-3) target cells modified to stably express firefly luciferase (ffLuc) were cultured for 3 days with NT, CD19-ENG (solid bar), or CLEC12A-ENG (striped bar) T cells. D-luciferin was added and live cell percentage determined by bioluminescent imaging. Cells normalized to those in NT T-cell condition. T cell:target cell ratio was 1:1. Dots representative of individual T-cell donors.
Figure 5B:
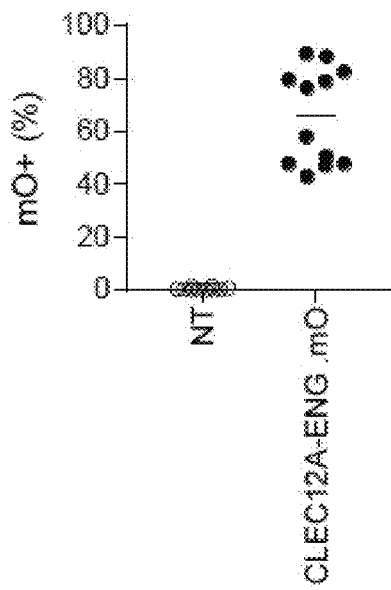

The CLEC12A-ENG construct was produced using GeneArt (ThermoScientific) gene synthesis of a CLEC12A-specific scFv (21.16)(Ref. 15; herein incorporated by reference in its entirety) which was then subcloned into a pSFG retroviral vector encoding a CD3E binding element and mOrange downstream of an IRES sequence (Ref. 16; herein incorporated by reference in its entirety)(FIG. 5A). A CD19-ENG construct was shared by Dr. Stephen Gottschalk (St. Jude Children's Research Hospital, Memphis, TN), also in a pSFG backbone (Ref. 17; herein incorporated by reference in its entirety). CD123.IL7Rα CAR constructs were generated using GeneArt (ThermoScientific) gene synthesis of a CD123-specific scFv (26292)(Ref. 18; herein incorporated by reference in its entirety) linked to an IgG1 hinge (GenBank: AAA58693.1) and the transmembrane and intracellular domain of IL7Rα (NCBI: NP_002176.2, amino acids 240-459). IL7Rα mutants were generated using the Q5 Site-directed mutagenesis kit (New England Biolabs, Ipswich, MA). Primers for mutagenesis were obtained from Integrated DNA Technologies (Skokie, Illinois, FIG. 11). All newly generated plasmids were verified by Sanger sequencing performed by the University of Michigan DNA Sequencing Core. RD114-pseudotyped retroviral particles were generated as previously described (Ref. 16; herein incorporated by reference in its entirety).

Generation of Engineered T Cells

Blood cells were purchased in the form of buffy coats (Carter BloodCare, Bedford, TX). Peripheral blood mononuclear cells (PBMCs) were isolated using a Ficoll density gradient and were then used according to a University of Michigan IRB-approved protocol. Cells were activated by stimulation on OKT3 (Miltenyi Biotec, Auburn, CA) and anti-CD28 (for co-stimulation, Becton Dickinson, Mountain View, CA) coated non-tissue culture-treated 24-well plates. Recombinant human IL 7 (10 ng/mL, preclinical bioreposiitory, National Cancer Institute, Frederick, MD) and IL15 (5 ng/mL, National Cancer Institute) were added to cultures on day 2, and the following day cells were transduced with retroviral particles immobilized on RetroNectin (Clontech Laborotories, Mountain View, CA). In experiments using luciferase expressing T cells, cells were transduced on subsequent days, first with the T-cell targeting moiety and second with the retrovirus carrying an enhanced GFP.firefly Luciferase fusion gene (Ref. 14; herein incorporated by reference in its entirety). T cells were maintained and expanded in the presence of IL7 and IL15. Cells were analyzed for expression of mOrange or artificial receptor by using flow cytometric analysis 5 to 7 days post-transduction.

Flow Cytometry

Fluorochrome conjugated isotype controls, anti-CD123, antiCLEC12A, anti-His, and anti-CD3 were purchased from BD Biosciences (San Jose, CA). Recombinant human CD123-His was produced by Sino Biological (Beijing, China). Analysis was performed on at least 20,000 cells per sample using an Attune NxT instrument (Thermo Scientific) and analyzed with FloJo software. Antigen quantification was performed using QuantiBrite beads (BD Biosciences) per manufacturer protocol. Each quantification was performed in triplicate.

Cytokine Secretion Assay

T cells were plated with target cells at a 1:1 ratio. Following 24 hours of culture, supernatant was harvested and analyzed for the presence of interferon (IFN)γ or IL2 using ELISA kits (R&D systems) according to the manufacturer's instruction. Percent relative change was calculated with formula $(Y-X)/X*100$.

Cytotoxicity Assay

Target cells containing stable expression of firefly luciferase were incubated with T cells at 1:1, 1:2, 1:5, and 1:10 effector to target (E:T) ratios. Targets in media alone were used for assessment of spontaneous death. After 18 hours of culture, bioluminescence was measured. Mean percentage of specific lysis of triplicate samples was calculated as $100*(\text{spontaneous death}-\text{experimental death})/(\text{spontaneous deathbackground})$. Cytotoxicity assays were incubated for 3 days: on day 0, cells were plated at a 1:1 E:T ratio. On day 3, cells were treated with Luciferin and bioluminescence was measured and compared to an identical condition containing unmodified T cells.

Xenograft Mouse Model

All animal experiments were conducted in accordance with and with the approval of the University of Michigan Institutional Animal Care and Use Committee (IACUC) .NSG (NOD.Cg-Prkdcscid/I12rgtm1Wjl/SzJ, Jackson Laboratory, Bar Harbor, ME) mice were engrafted with AML cell lines (MV-4-11, MV-4-11.ffLuc, OCI-AML-3.ffLuc) via intravenous tail vein injection. One week following leukemia injection, mice were given 106 unmodified or modified T cells, as described. Mice were followed weekly with bioluminescent imaging. Animals were imaged using the IVIS system (IVIS, Xenogen Corp.) 10 minutes after intraperitoneal injection of DLuciferin (ThermoFisher Scientific). Images were analyzed using Living Image 4.5.1 software (PerkinElmer, Waltham, MA). Peripheral blood was drawn via the facial vein and analyzed via FACS. Mice were euthanized when they either lost >20% of body weight, exhibited hind leg paralysis, or were otherwise deemed of clinical concern in collaboration with the veterinary team of the University of Michigan Unit for Laboratory Animal Medicine.

Colony Forming Unit (CFU) assays. Healthy donor bone marrow was obtained under a University of Michigan IRB approved protocol. Bone marrow mononuclear cells (BMMCs) were isolated by standard density gradient centrifugation and cyropreserved. BMMCs were incubated with media alone, unmodified, or modified T cells as described at a 5:1 E:T ratio for 6 hours, then plated in MethoCult (Classic) media (Stemcell Technologies, Vancouver, BC, Canada) per manufacturer's instruction. After 10-14 days, colonies were manually counted.

Western Blot

T cells were plated overnight in RPMI+10% FBS and glutamax without additional cytokine. T cells were lysed in radioimmunoprecipitation assay (RIPA) lysis buffer with protease (cOmplete) and phosphatase (PhosSTOP) inhibitor cocktails (MilliporeSigma, St. Louis, MO) on ice. Electrophoresis was conducted using Novex™ WedgeWell™ 10% Bis-Tris Mini Gels (ThermoFisher) and protein transferred to polyvinylidene difluoride (PVDF) membrane. Western blot analysis was performed with the following antibodies: rabbit anti-human p-STAT5 (clone D47E7, Cell Signaling), STAT5 (clone D2605, Cell Signaling), and GAPDH (clone 6C5, Invitrogen).

Statistical Analysis

GraphPad Prism 7 software (GraphPad Software, La Jolla, CA) was used for statistical analysis. Measurement data were presented using descriptive statistics as noted in text, including, mean, median, range, ±standard error. For comparison between two groups, two-tailed t-test was used with correction for multiple comparisons using the Holm-Sidak method. For comparisons including more than two groups, two-way analysis of variance (ANOVA) corrected for comparison using the method of Sidek was incorporated. Survival of mice was estimated by the Kaplan-Meier method and differences in survival between groups were calculated by the Logrank (Mantel-Cox) and Gehan-Breslow-Wilcoxon test.

Results

CLEC12A-ENG T Cells Recognize and Kill CLEC12A+ AML Targets

A γ-retroviral construct containing the coding sequence of a CLEC12AxCD3 bispecific engager molecule (CLEC12A-ENG) and that of the fluorescent protein mOrange was designed and synthesized (FIG. 5A). Retroviral transduction of primary activated T cells was used to induce constitutive production and secretion of CLEC12A-ENG. In order to verify T-cell modification, cells were analyzed via FACS for expression of mOrange. Reproducible transduction efficiencies were achieved (FIG. 5B, Median: 67.5%, Range 43.2-

Figure 5C:
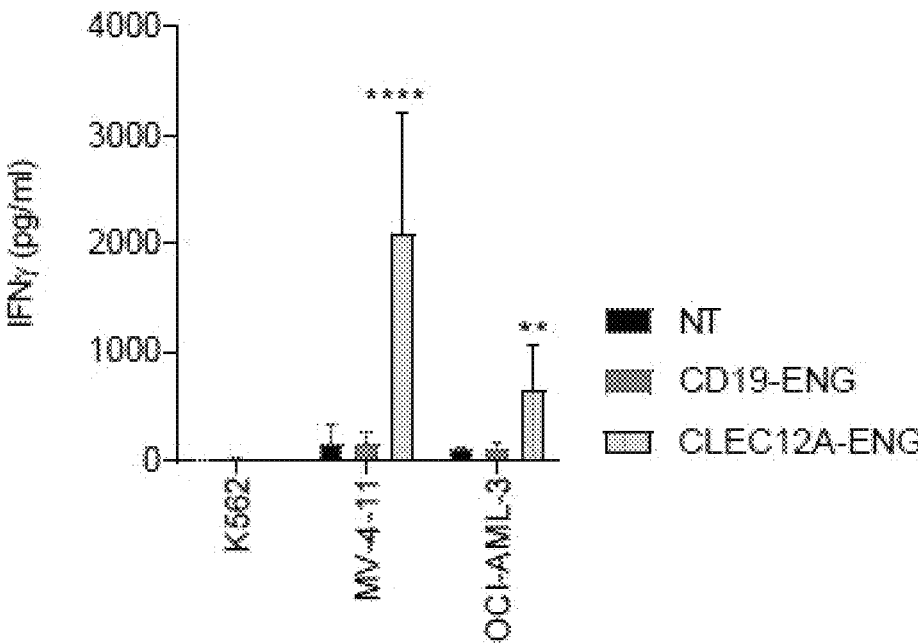
Figure 5D:
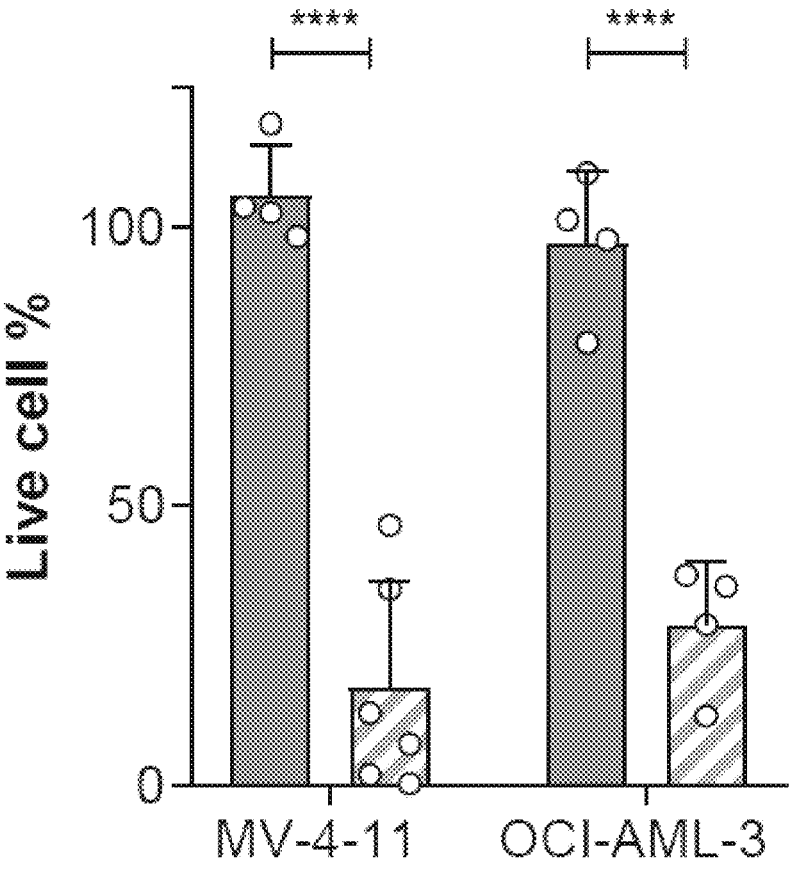

89.6%, n=12 independent T-cell donors). CLEC12A expression on a panel of AML cell lines (MV-4-11, OCI-AML-3, Molm-13) was measured with FACS analysis. CLEC12A expression was variable between the tested lines, and overall was found to be less than 5000 molecules/cell (FIG. 12). Despite this relatively low surface expression, CLEC12A-ENG T cells were specifically activated by CLEC12A+ target cells (MV-4-11, OCI-AML-3) as measured by IFNγ secretion. T cells engineered to secrete a bispecific engager molecule targeted to the antigen CD19 (CD19-ENG) were not activated by target cells. Similarly, CLEC12A-ENG T cells were not activated by the CLEC12A− K562 cell line (FIG. 5C). CLEC12A-ENG T cells were also found to be specifically cytotoxic to CLEC12A+ AML cells (FIG. 5D).

CLEC12A-ENG T Cells Demonstrate Specific In Vivo Antitumor Activity

Figure 13:
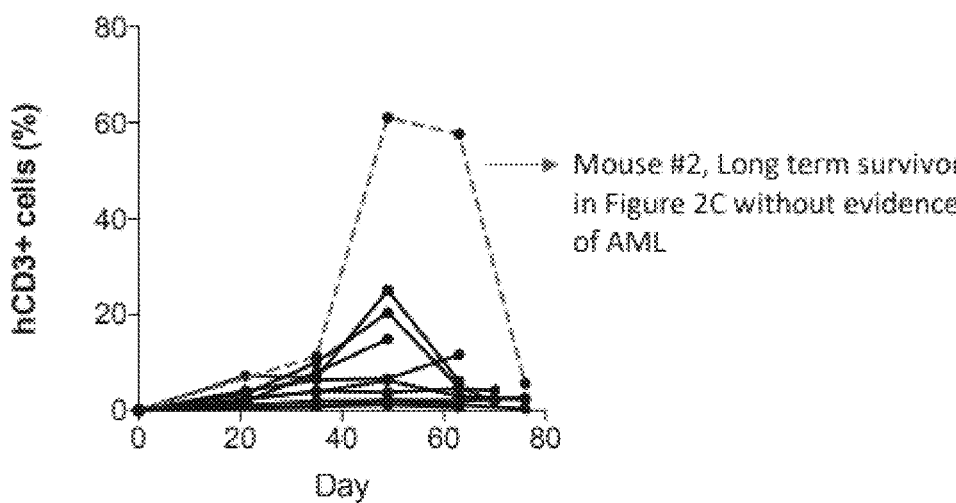
FIG. 13. CLEC12A-ENG T cell expansion in MV-4-11.ffLuc engrafted mice. Murine peripheral blood was collected, RBCs lysed, and remaining cells stained with hCD3 antibody. Data analyzed by FACS. Mouse #2 in cohort 1 of MV-4-11.ffLuc xenograft studies exhibited significantly enhanced human T cell expansion between D49 and 63.

In order to evaluate in vivo antitumor activity of CLEC12A-ENG T cells, a human xenograft mouse model was established in NOD.Cg-PrkdcscidIL2rgtm1Wjl/SzJ (NSG) mice. The human CLEC12A+ AML cell line, MV-4-11, was first modified to stably express firefly luciferase (ffLuc). These cells were then used to engraft NSG mice via tail vein injection. One week following leukemia injection, mice received control T cells or CLEC12A-ENG T cells (FIG. 6A). Leukemic progression was monitored by bioluminescence imaging following intraperitoneal injection of D-Luciferin. CLEC12A-ENG T cells demonstrated antitumor efficacy that led to improved median survival in treated mice (FIG. 6B-D). Murine peripheral blood (PB) was monitored every 2 weeks starting on day 21 or 35 post-AML injection. Analysis of initial cohorts of mice treated with CLEC12A-ENG T cells indicates correlation of antitumor responsiveness to T-cell expansion in PB. A mouse that remained disease-free for the course of the experiment demonstrated enhanced T-cell expansion and persistence, primarily between days 49 and 63 (FIG. 13).

Cytotoxicity Unaffected by Co-Expression of CD123.IL7Ra and CLEC12A-ENG

Figure 14:
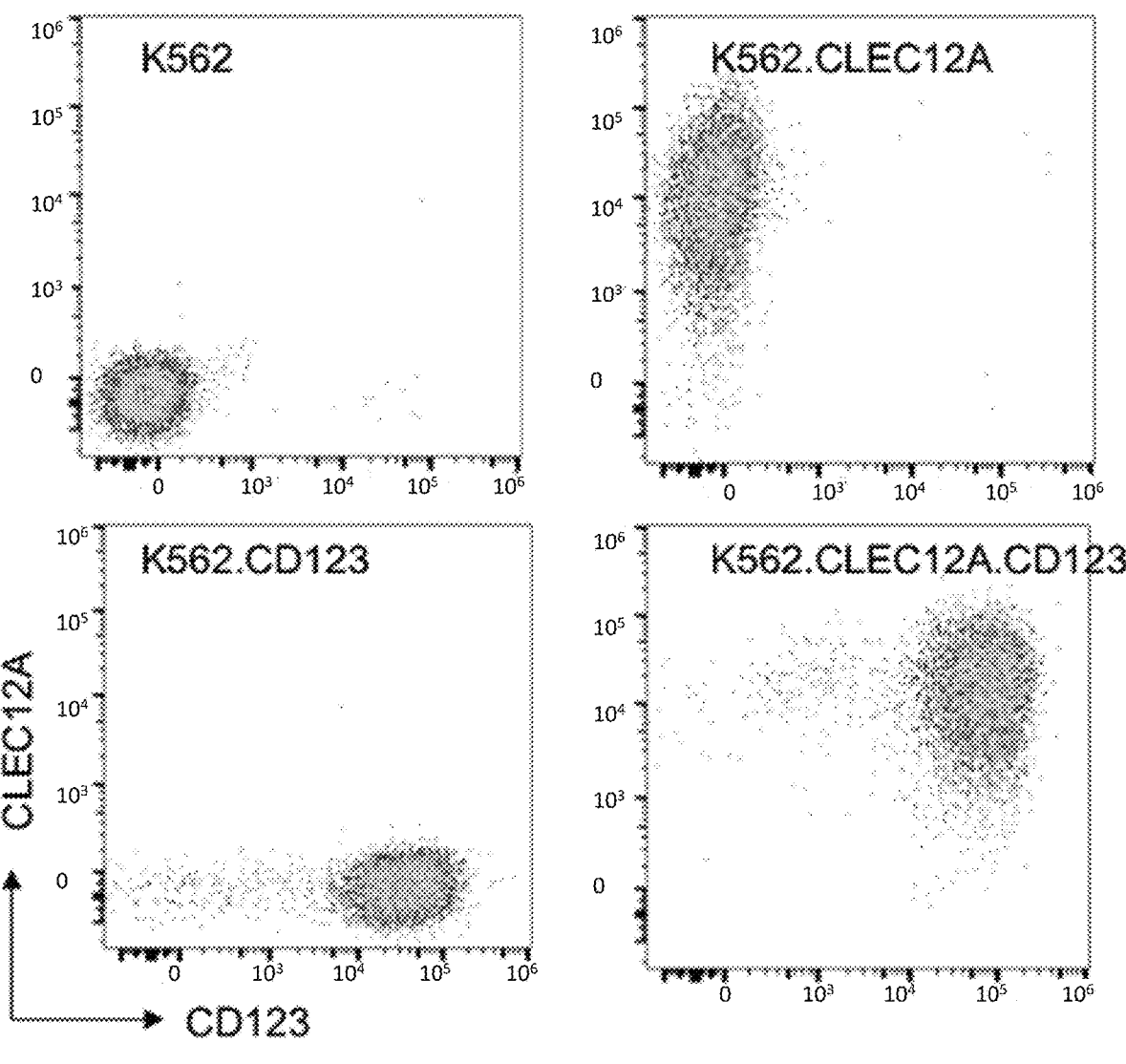
FIG. 14. K562 can be effectively modified to express CLEC12A and CD123. Lentiviral targeting vectors were designed to encode either CLEC12A or CD123. The K562 cell line was transduced with lentiviral vector, sorted for antigen expression, and expression verified with FACS analysis.

Although CLEC12A-ENG T cells had anti-AML activity, leukemia eventually progressed. It was therefore asked whether provision of signal 3 in the form of a chimeric IL7Rα could improve the anti-AML activity of CLEC12A-ENG T cells. A chimeric receptor composed of an extracellular domain consisting of a scFv specific for the AMLassociated antigen CD123 (Refs. 16,18; herein incorporated by reference in their entireties) and the transmembrane and intracellular domains of IL7Rα was designed (CD123.IL7Rα; FIG. 7A). Cells were either single transduced with retroviral vectors encoding CLEC12A-ENG or CD123.IL7Ra, or double transduced with both vectors simultaneously. Single transduction resulted in a median of 60% ENG+ and 54.5% CD123.IL7Rα+ cells (range 56-81% and 36.1-66.6%, respectively). Double transduction resulted in a median of 22.7% ENG+(range: 17.5-29.9%), 24.9% CD123.IL7Rα+ (range: 11.9-30.6%), and 25.9% double positive cells (range: 19.8-38.7%, FIG. 7B). The CLEC12A-ENG construct was further modified (FIG. 5A), replacing the mOrange sequence with our CD123.IL7Rα to allow for expression of both synthetic proteins after a single transduction. To assess inhibition of antigen-dependent cytotoxicity in CLEC12A-ENG.CD123IL7Rα T cells, effector cells were cocultured with targets expressing either CD123 or CLEC12A alone, or both antigens together (FIG. 14). Coexpression of CD123.IL7Rα with the CLEC12A-ENG did not diminish the CLEC12A− specific cytotoxicity. In a short-term cytotoxicity assay, both CLEC12A-ENG and CLEC12A-ENG.CD123IL7Rα T cells were equally effective at killing target cells expressing CLEC12A (FIG. 7C). Additional cytotoxicity secondary to CD123 binding by CD123.IL7Rα was not observed. Expression of CD123.IL7Rα did not cause toxicity to hematopoietic progenitor cells at a high (5:1) E:T ratio (FIG. 7D). T cells engineered to secrete a bispecific CD123×CD3 molecule (CD123-ENG) were used as a positive control for progenitor cell toxicity due to CD123 binding.

IL7Rα Signaling and CD123 Binding Enhance CD123.IL7Ra T-Cell Activation.

Figure 8A:
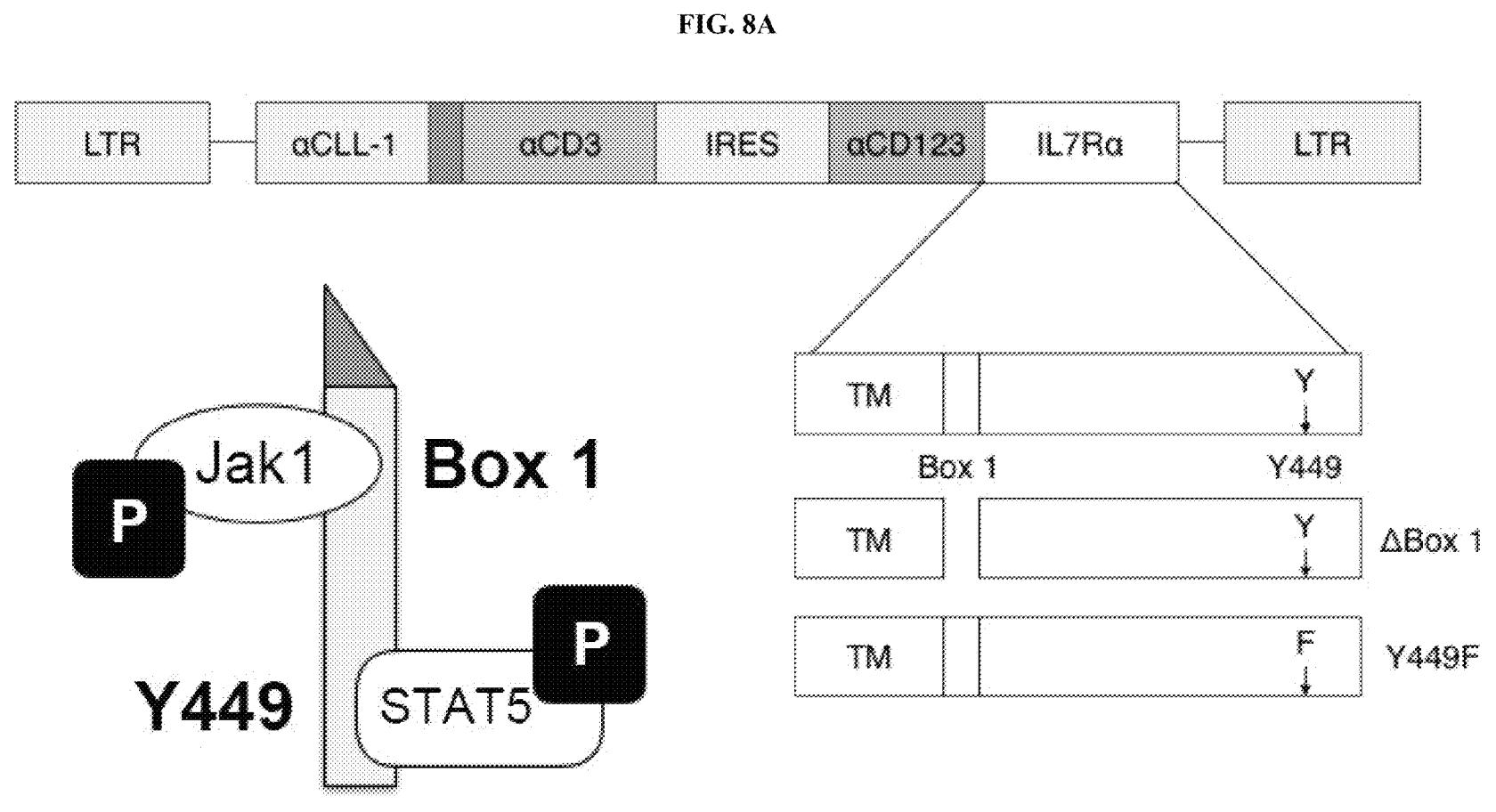
Figure 8B:
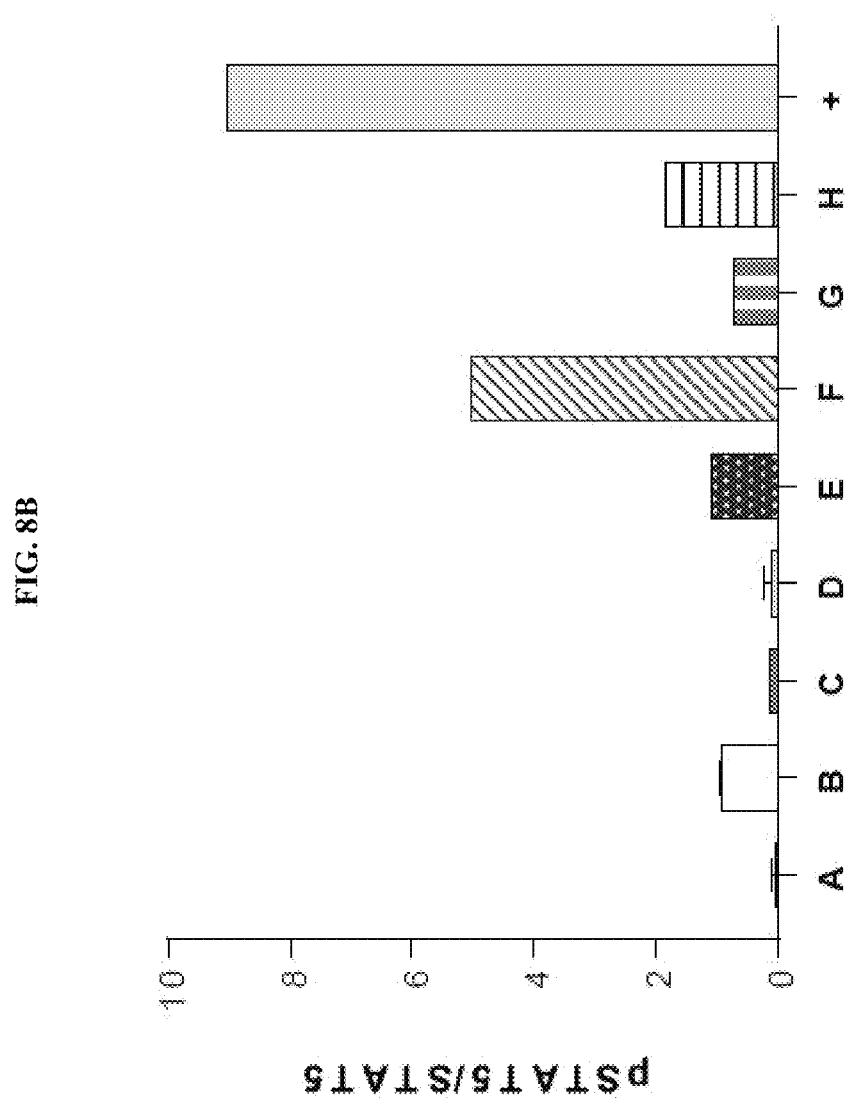
Figure 8C:
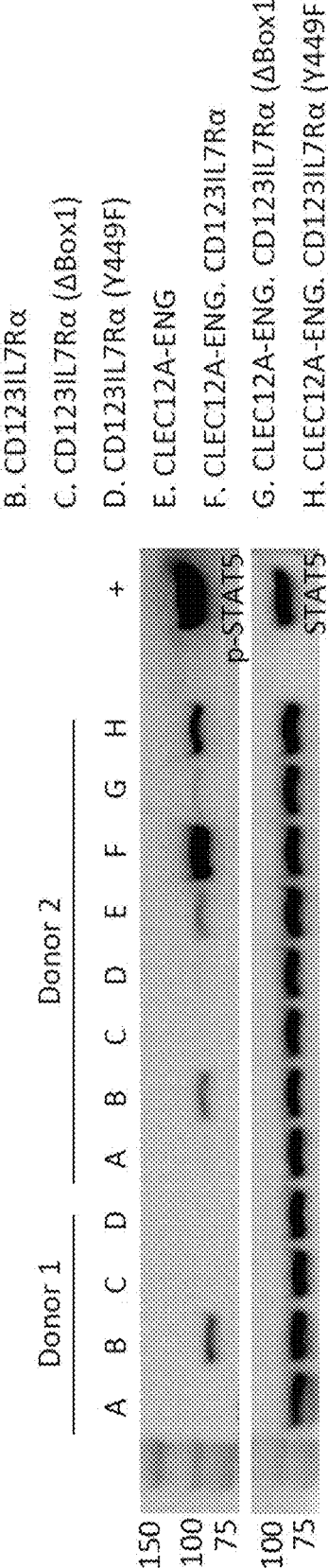

To test for intact IL7Rα signaling, two additional chimeric receptors were created. In one, Box 1 is deleted to prevent Jak1 binding (CD123.IL7Rα.ΔBox1). In a second molecule, tyrosine 449 is mutated to phenylalanine (Y449F), which prevents Y449 phosphorylation and subsequent STAT5 binding (CD123.IL7Rα.Y449F; FIG. 8A).(19-22) STAT5 phosphorylation was evaluated in T cells expressing the three CD123.IL7Rα with Western blotting. Independent of binding to CD123, constitutive STAT5 phosphorylation was observed in T cells expressing unmutated chimeric IL7Rα (FIG. 8B,C). Deletion of Box1 or mutation of Y449 to phenylalanine (Y449F) rendered p-STAT5 undetectable. In cells expressing CLEC12A-ENG, CD123.IL7Rα expression increased pSTAT5 levels. IL7Rα mutation reduced STAT5 phosphorylation (FIG. 8B,C). Therefore, CD123.IL7Rα expression induces downstream STAT5 phosphorylation dependent on known motifs in the corresponding endogenous IL7R.

Figure 9A:
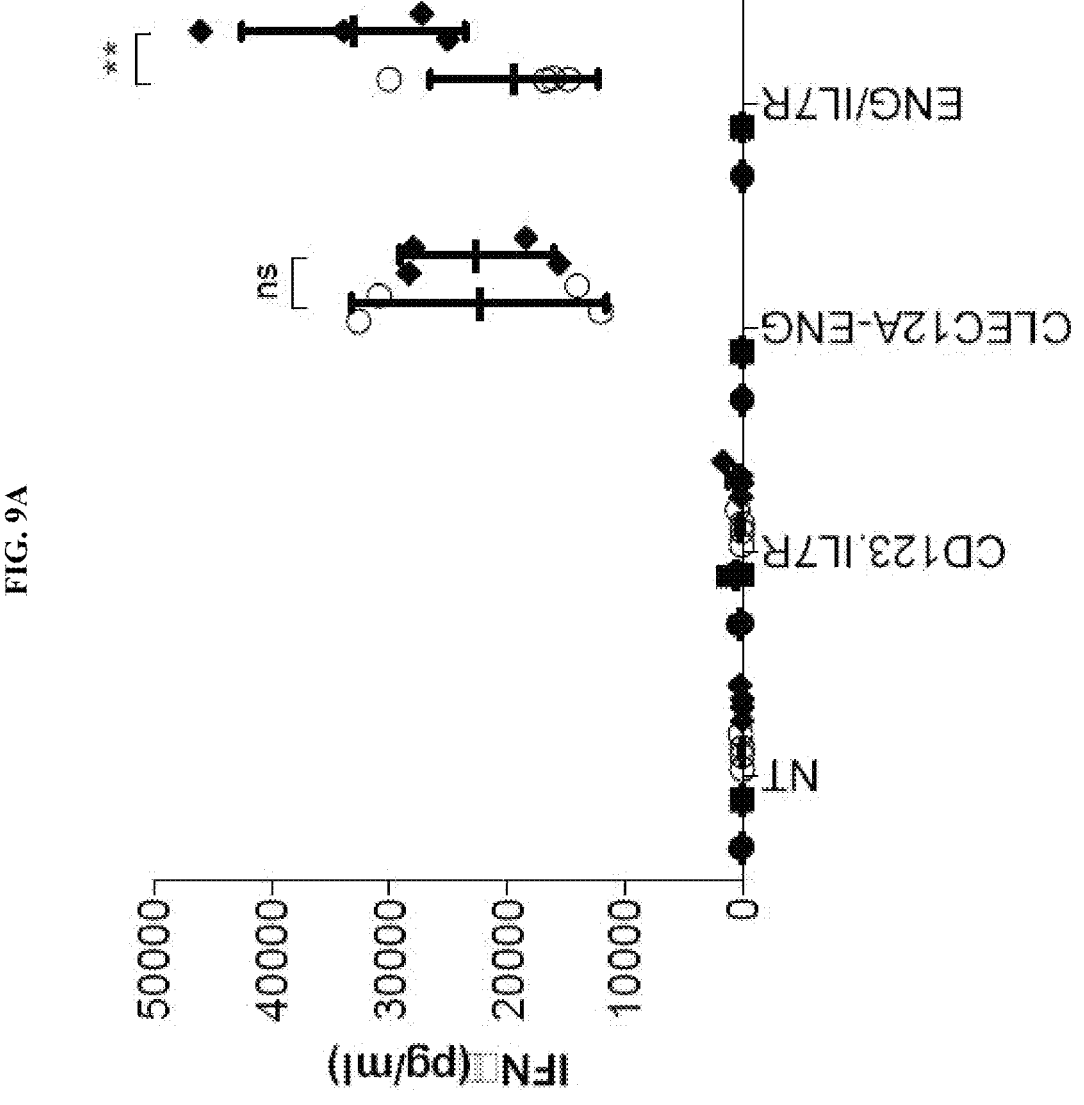
FIGS. 9A-C. Enhanced CLEC12A-ENG.CD123IL7Rα T-cell activation is secondary to CD123+ target recognition and intact IL7Rα elements. A. IFNγ and B. IL2 secreted into supernatant following culture of indicated effector and target cells. C. Relative change in IFNγ secretion in T cells cultured with K562.CLEC12A vs. K562.CLEC12A.CD123.
Figure 9B:
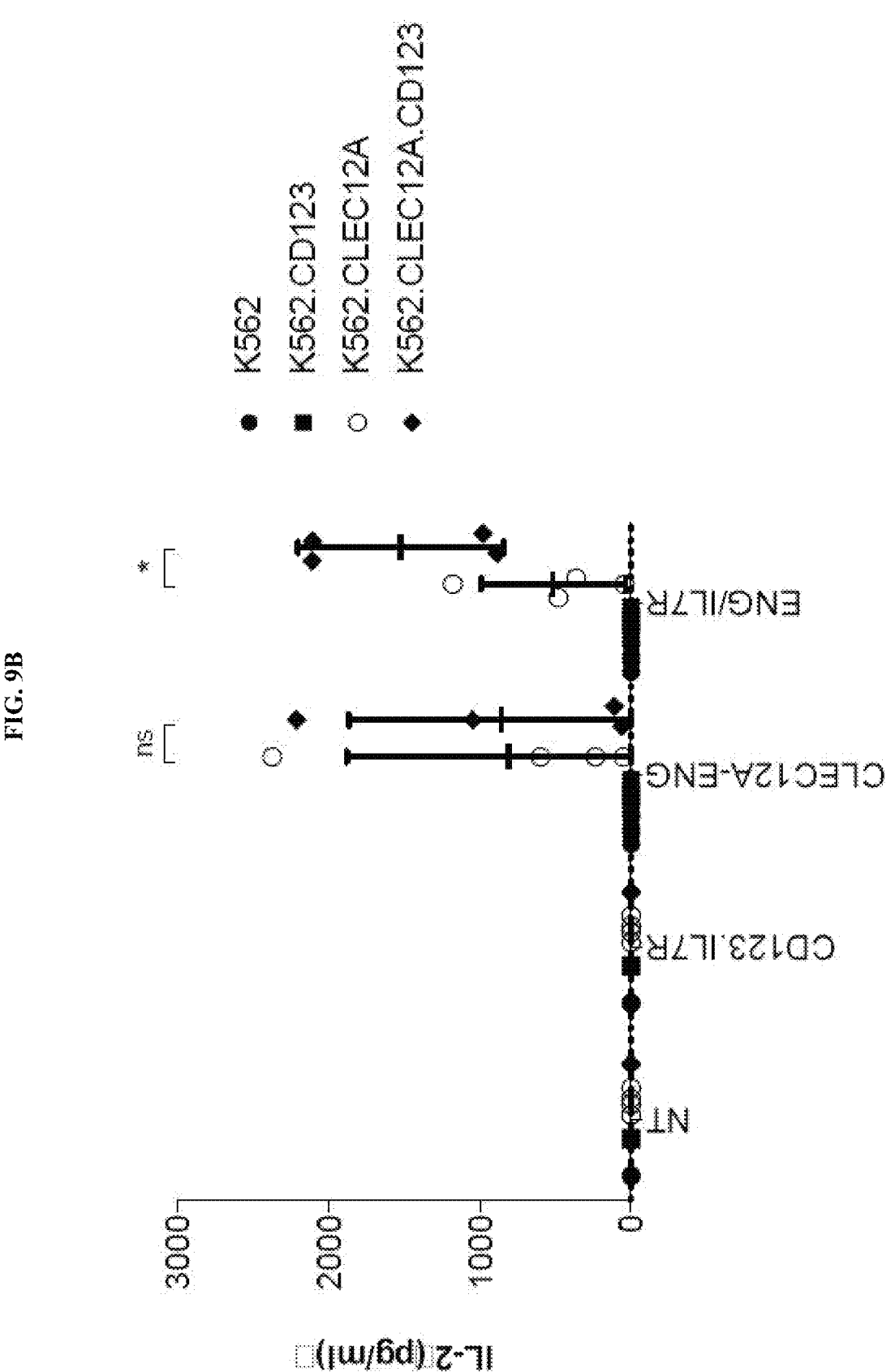
Figure 9C:
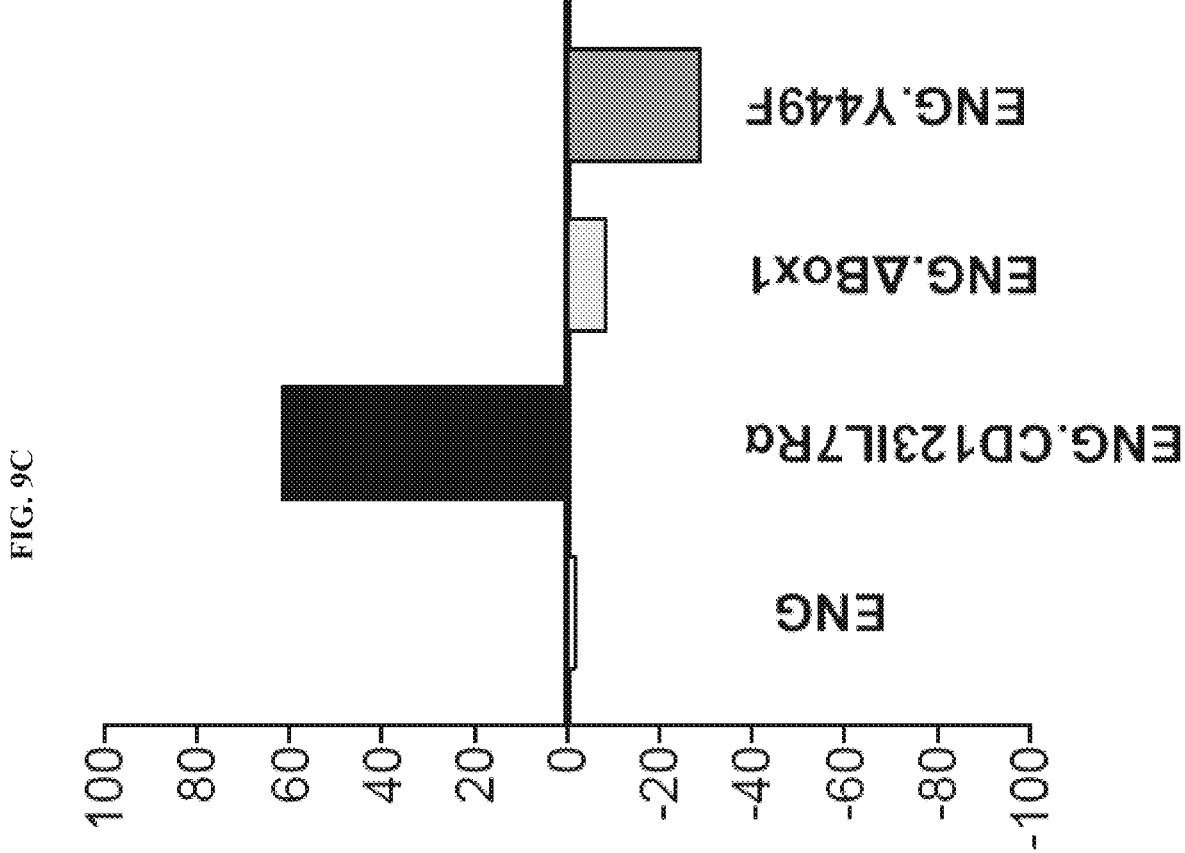

To assess functional activation, effector cells were cultured with targets expressing either CD123 or CLEC12A alone, or both antigens together (FIG. 14). CLEC12A–ENG.CD123IL7Rα T cells were stimulated to secrete more cytokine when challenged with targets expressing both CLEC12A and CD123 (FIG. 9A,B). In contrast, the presence of the CD123 target antigen did not stimulate additional IFNγ or 2 secretion by CLEC12A-ENG cells. Use of our CD123.IL7Rα mutants diminished this augmented T-cell activation state (FIG. 9C). T cells expressing CLEC12A-ENG and CD123.IL7Rα secrete more inflammatory cytokine when target cells express both CLEC12A and CD123. CLEC12A-ENG T secrete the same amount of cytokine regardless of target cell CD123 expression. Mutation of certain CD123.IL7Rα elements prevented optimal T-cell activation following dual-target recognition.

CLEC12A-ENG.CD123IL7Rα T Cells have Improved In Vivo Expansion and Efficacy

Figure 10B:
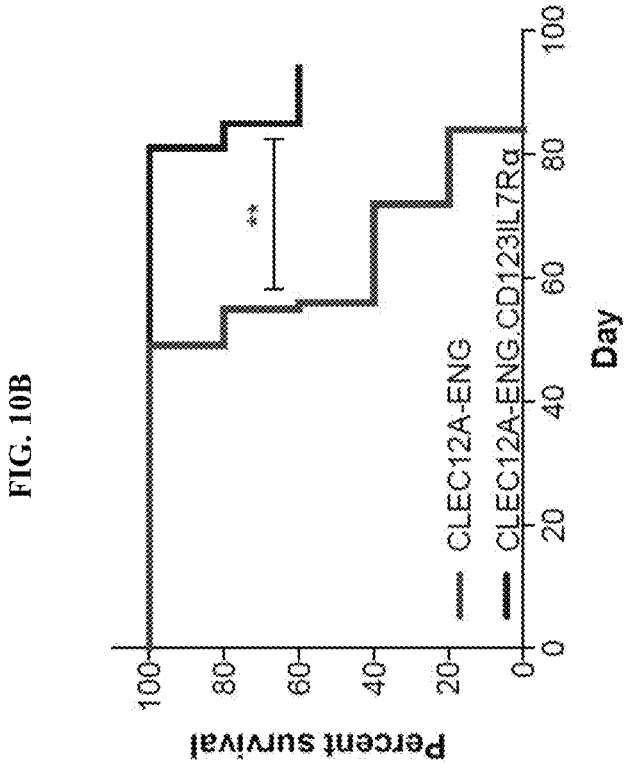
FIGS. 10A-C. CD123.IL7Rα T cells have improved expansion and in vivo anti-leukemia control. A. T cells were transduced with ffLuc to enable tracking of expansion and persistence vs. unlabeled MV-4-11. (n=5 mice each group, one T-cell donor used for cohort; Solid line: mean, dotted lines: individual mice). B. Kaplan-Meier survival analysis, Median survival: CLEC12A-ENG—56 days, CLEC12A-ENG.CD123IL7Rα—undefined. C. Representative images of mice.
Figure 10A:
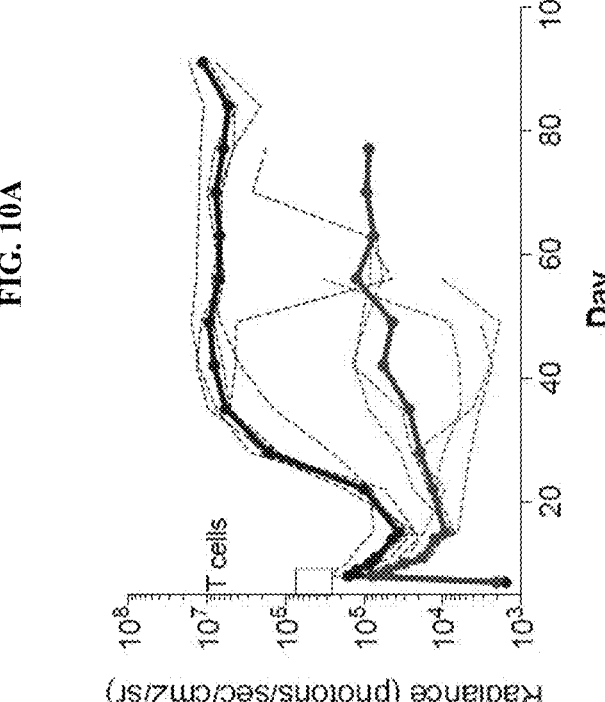
Figure 10C:
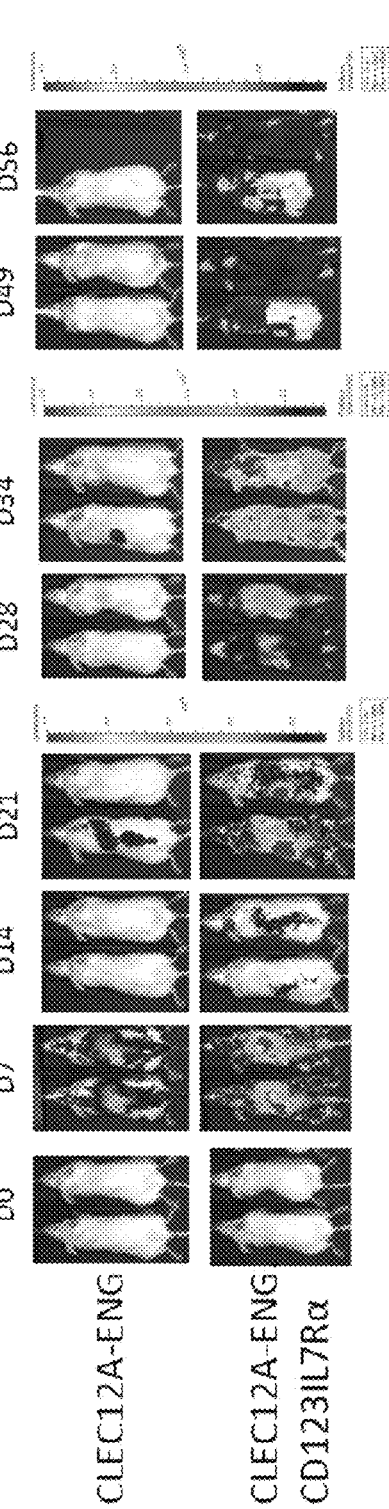

To evaluate the capacity for the CD123.IL7Rα to improve CLEC12A-ENG T-cell expansion and antitumor activity in vivo, a CLEC12A+/CD123+MV-4-11 xenograft model was used. To facilitate T-cell tracking, ffLuc expression was engineered in CLEC12A-ENG and CLEC12A-ENG.CD123IL7Rα T cells (FIG. 15). Both T-cell expansion and overall survival were enhanced in mice treated with CLEC12A-ENG.CD123IL7Rα T cells as compared to animals treated with CLEC12AENG T cells (median overall survival: not reached vs. 56 days, FIG. 10A-C). Improved survival in CLEC12A-ENG.CD123IL7Rα treated mice was also seen in a second AML xenograft using OCI-AML-3.ffLuc leukemia cells. The MV-4-11.ffLuc AML model indicates a trend (FIG. 16). Given the different overall survival seen in mice engrafted with MV-4-11.ffLuc as compared to those engrafted with unmodified MV-4-11, the lines were tested for phenotypic differences. Decreased expression of CLEC12A in the MV-4-11 cell line was observed (FIG. 17).

All publications and patents provided herein incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

The following references, some of which are cited above by number, are herein incorporated by reference in their entireties.

1. Zwaan C M, Kolb E A, Reinhardt D, Abrahamsson J, Adachi S, Aplenc R, et al. Collaborative Efforts Driving Progress in Pediatric Acute Myeloid Leukemia. J Clin Oncol 2015; 33:2949-62
2. O'Donnell M R, Tallman M S, Abboud C N, Altman J K, Appelbaum F R, Arber D A, et al. Acute Myeloid Leukemia, Version 3.2017, NCCN Clinical Practice Guidelines in Oncology. J Natl Compr Canc Netw 2017; 15:926-57
3. Appelbaum F R, Gundacker H, Head D R, Slovak M L, Willman C L, Godwin J E, et al. Age and acute myeloid leukemia. Blood 2006; 107:3481-5
4. Institute NC. Cancer Stat Facts: Acute Myeloid Leukemia (AML). https://seer.cancer.gov/statfacts/html/amyl.html2011-2015.
5. Perna F, Berman S H, Soni R K, Mansilla-Soto J, Eyquem J, Hamieh M, et al. Integrating Proteomics and Transcriptomics for Systematic Combinatorial Chimeric Antigen Receptor Therapy of AML. Cancer Cell 2017; 32:506-19 e5
6. Bonifant C L, Velasquez M P, Gottschalk S. Advances in immunotherapy for pediatric acute myeloid leukemia. Expert Opin Biol Ther 2018; 18:51-63
7. Munoz L, Nomdedeu J F, Lopez O, Carnicer M J, Bellido M, Aventin A, et al. Interleukin-3 receptor alpha chain (CD123) is widely expressed in hematologic malignancies. Haematologica 2001; 86:1261-9
8. Bakker A B, van den Oudenrijn S, Bakker A Q, Feller N, van Meijer M, Bia J A, et al. Ctype lectin-like molecule-1: a novel myeloid cell surface marker associated with acute myeloid leukemia. Cancer Res 2004; 64:8443-50
9. van Rhenen A, van Dongen G A, Kelder A, Rombouts E J, Feller N, Moshaver B, et al. The novel AML stem cell associated antigen CLL-1 aids in discrimination between normal and leukemic stem cells. Blood 2007; 110:2659-66
10. Maude S L, Frey N, Shaw P A, Aplenc R, Barrett D M, Bunin N J, et al. Chimeric antigen receptor T cells for sustained remissions in leukemia. N Engl J Med 2014; 371:1507-17
11. Porter D L, Hwang W T, Frey N V, Lacey S F, Shaw P A, Loren A W, et al. Chimeric antigen receptor T cells persist and induce sustained remissions in relapsed refractory chronic lymphocytic leukemia. Sci Transl Med 2015; 7:303ra139
12. Surh C D, Sprent J. Homeostasis of naive and memory T cells. Immunity 2008; 29:848-62
13. Takada K, Jameson S C. Naive T cell homeostasis: from awareness of space to a sense of place. Nat Rev Immunol 2009; 9:823-32

14. Vera J, Savoldo B, Vigouroux S, Biagi E, Pule M, Rossig C, et al. T lymphocytes redirected against the kappa light chain of human immunoglobulin efficiently kill mature B lymphocyte-derived malignant cells. Blood 2006; 108: 3890-7

15. Zhao X, Singh S, Pardoux C, Zhao J, Hsi E D, Abo A, et al. Targeting C-type lectin-like molecule-1 for antibody-mediated immunotherapy in acute myeloid leukemia. Haematologica 2010; 95:71-8

16. Bonifant C L, Szoor A, Torres D, Joseph N, Velasquez M P, Iwahori K, et al. CD123-Engager T Cells as a Novel Immunotherapeutic for Acute Myeloid Leukemia. Mol Ther 2016; 24:1615-26

17. Velasquez M P, Torres D, Iwahori K, Kakarla S, Arber C, Rodriguez-Cruz T, et al. T cells expressing CD19-specific Engager Molecules for the Immunotherapy of CD19-positive Malignancies. Sci Rep 2016; 6: 27130

18. Du X, Ho M, Pastan I. New immunotoxins targeting CD123, a stem cell antigen on acute myeloid leukemia cells. J Immunother 2007; 30:607-13

19. Venkitaraman A R, Cowling R J. Interleukin-7 induces the association of phosphatidylinositol 3-kinase with the alpha chain of the interleukin-7 receptor. Eur J Immunol 1994; 24:2168-74

20. Lin J X, Migone T S, Tsang M, Friedmann M, Weatherbee J A, Zhou L, et al. The role of shared receptor motifs and common Stat proteins in the generation of cytokine pleiotropy and redundancy by IL-2, IL-4, IL-7, IL-13, and IL-15. Immunity 1995; 2:331-9

21. Jiang Q, Li W Q, Hofmeister R R, Young H A, Hodge D R, Keller J R, et al. Distinct regions of the interleukin-7 receptor regulate different Bcl2 family members. Mol Cell Biol 2004; 24:6501-13

22. Rosenthal L A, Winestock K D, Finbloom D S. IL-2 and IL-7 induce heterodimerization of STAT5 isoforms in human peripheral blood T lymphoblasts. Cell Immunol 1997; 181:172-81

23. Taussig D C, Pearce D J, Simpson C, Rohatiner A Z, Lister T A, Kelly G, et al. Hematopoietic stem cells express multiple myeloid markers: implications for the origin and targeted therapy of acute myeloid leukemia. Blood 2005; 106:4086-92

24. Bill M, P BvKN, P S W, Laine Herborg L, Stidsholt Roug A, Hokland P, et al. Mapping the CLEC12A expression on myeloid progenitors in normal bone marrow; implications for understanding CLEC12A-related cancer stem cell biology. J Cell Mol Med 2018; 22:2311-8

25. Tashiro H, Sauer T, Shum T, Parikh K, Mamonkin M, Omer B, et al. Treatment of Acute Myeloid Leukemia with T Cells Expressing Chimeric Antigen Receptors Directed to Ctype Lectin-like Molecule 1. Mol Ther 2017; 25:2202-13

26. Laborda E, Mazagova M, Shao S, Wang X, Quirino H, Woods A K, et al. Development of A Chimeric Antigen Receptor Targeting C-Type Lectin-Like Molecule-1 for Human Acute Myeloid Leukemia. Int J Mol Sci 2017; 18

27. Wang J, Chen S, Xiao W, Li W, Wang L, Yang S, et al. CAR-T cells targeting CLL-1 as an approach to treat acute myeloid leukemia. J Hematol Oncol 2018; 11:7

28. Korpelainen E I, Gamble J R, Vadas M A, Lopez A F. IL-3 receptor expression, regulation and function in cells of the vasculature. Immunol Cell Biol 1996; 74:1-7

29. Korpelainen E I, Gamble J R, Smith W B, Dottore M, Vadas M A, Lopez A F. Interferongamma upregulates interleukin-3 (IL-3) receptor expression in human endothelial cells and synergizes with IL-3 in stimulating 30. Pizzitola I, Anjos-Afonso F, Rouault-Pierre K, Lassailly F, Tettamanti S, Spinelli O, et al. Chimeric antigen receptors against CD33/CD123 antigens efficiently target primary acute myeloid leukemia cells in vivo. Leukemia 2014; 28:1596-605

31. Gill S, Tasian S K, Ruella M, Shestova O, Li Y, Porter D L, et al. Preclinical targeting of human acute myeloid leukemia and myeloablation using chimeric antigen receptormodified T cells. Blood 2014; 123:2343-54

32. Deshpande P, Cavanagh M M, Le Saux S, Singh K, Weyand C M, Goronzy J J. IL-7- and IL-15-mediated TCR sensitization enables T cell responses to self-antigens. J Immunol 2013; 190:1416-23

33. Cho J H, Kim H O, Surh C D, Sprent J. T cell receptor-dependent regulation of lipid rafts controls naive CD8+ T cell homeostasis. Immunity 2010; 32:214-26

34. Alvarez-Vallina L, Russell S J. Efficient discrimination between different densities of target antigen by tetracycline-regulatable T bodies. Hum Gene Ther 1999; 10:559-63

35. Chmielewski M, Hombach A, Heuser C, Adams G P, Abken H. T cell activation by antibody-like immunoreceptors: increase in affinity of the single-chain fragment domain above threshold does not increase T cell activation against antigen-positive target cells but decreases selectivity. J Immunol 2004; 173:7647-53

36. Turatti F, Figini M, Balladore E, Alberti P, Casalini P, Marks J D, et al. Redirected activity of human antitumor chimeric immune receptors is governed by antigen and receptor expression levels and affinity of interaction. J Immunother 2007; 30:684-93

37. Fry T J, Shah N N, Orentas R J, Stetler-Stevenson M, Yuan C M, Ramakrishna S, et al. CD22-targeted CAR T cells induce remission in B-ALL that is naive or resistant to CD19-targeted CAR immunotherapy. Nat Med 2018; 24:20-8

38. Shum T, Omer B, Tashiro H, Kruse R L, Wagner D L, Parikh K, et al. Constitutive Signaling from an Engineered IL7 Receptor Promotes Durable Tumor Elimination by Tumor-Redirected T Cells. Cancer Discov 2017; 7:1238-47

39. Mohammed S, Sukumaran S, Bajgain P, Watanabe N, Heslop H E, Rooney C M, et al. Improving Chimeric Antigen Receptor-Modified T Cell Function by Reversing the Immunosuppressive Tumor Microenvironment of Pancreatic Cancer. Mol Ther 2017; 25:249-58

40. Zhao Z, Condomines M, van der Stegen S J C, Perna F, Kloss C C, Gunset G, et al. Structural Design of Engineered Costimulation Determines Tumor Rejection Kinetics and Persistence of CAR T Cells. Cancer Cell 2015; 28:415-28

41. Stephan M T, Ponomarev V, Brentjens R J, Chang A H, Dobrenkov K V, Heller G, et al. T cell-encoded CD80 and 4-1BBL induce auto- and transcostimulation, resulting in potent tumor rejection. Nat Med 2007; 13:1440-9

42. Kloss C C, Condomines M, Cartellieri M, Bachmann M, Sadelain M. Combinatorial antigen recognition with balanced signaling promotes selective tumor eradication by engineered T cells. Nat Biotechnol 2013; 31:71-5

43. Velasquez M P, Szoor A, Vaidya A, Thakkar A, Nguyen P, Wu M F, et al. CD28 and 41BB Costimulation Enhances the Effector Function of CD19-Specific Engager T Cells. Cancer Immunol Res 2017; 5:860-70 major histocompatibility complex class II expression and cytokine production. Blood 1995; 86:176-82

SEQUENCES
IL7Ra (SEQ ID NO: 1)
MTILGTTFGMVFSLLQVVSGESGYAQNGDLEDAELDDYSFSCYSQLEV

NGSQHSLTCAFEDPDVNTTNLEFEICGALVEVKCLNFRKLQEIYFIET

KKFLLIGKSNICVKVGEKSLTCKKIDLTTIVKPEAPFDLSVIYREGAN

DFVVTFNTSHLQKKYVKVLMHDVAYRQEKDENKWTHVNLSSTKLTLLQ

RKLQPAAMYEIKVRSIPDHYFKGFWSEWSPSYYFRTPEINNSSGEMDP

ILLTISILSFFSVALLVILACVLWKKRIKPIVWPSLPDHKKTLEHLCK

KPRKNLNVSFNPESFLDCQIHRVDDIQARDEVEGFLQDTFPQQLEESE

KQRLGGDVQSPNCPSEDVVITPESFGRDSSLTCLAGNVSACDAPILSS

SRSLDCRESGKNGPHVYQDLLLSLGTTNSTLPPPFSLQSGILTLNPVA

QGQPILTSLGSNQEEAYVTMSSFYQNQ

IL7Ra transmembrane domain (SEQ ID NO: 2)
CCAATCCTGCTGACAATCAGCATCCTGAGCTTTTTCAGCGTGGCCCTG

CTGGTCATTCTGGCCGTGCTGTGG

IL7Ra transmembrane domain (SEQ ID NO: 3)
CCAATCCTGCTGATAATCAGCATCCTGAGCTTTTTCAGCGTGGCCCTG

CTGGTCATTCTGGCCGTGCTGTGG

IL7Ra intracellular signaling domain (SEQ ID NO: 4)
AAGAAGCGGATCAAGCCTATCGTGTGGCCCAGCCTGCCTGACCACAAA

AAGACCCTGGAACACCTGTGCAAGAAGCCCCGGAAGAACCTGAACGTG

TCCTTCAATCCCGAGAGCTTCCTGGACTGTCAGATTCACAGAGTGGAC

GACATCCAGGCCAGAGATGAGGTGGAAGGCTTTCTGCAGGACACATTC

CCTCAGCAGCTGGAAGAGAGCGAGAAGCAGAGACTCGGCGGAGATGTG

CAGTCCCCTAATTGCCCTAGCGAGGACGTCGTGATCACCCCTGAGAGC

TTCGGCAGAGATAGCTCCCTGACATGTCTGGCCGGCAATGTGTCCGCC

-continued
TGTGATGCCCCTATCCTGAGCAGCTCCAGAAGCCTGGATTGCAGAGAG

AGCGGCAAGAACGGCCCTCACGTGTACCAAGATCTGCTGCTGAGCCTG

GGCACCACCAATTCTACACTGCCTCCACCATTCAGCCTGCAGAGCGGC

ATCCTGACACTGAACCCTGTTGCTCAGGGCCAGCCAATCCTGACAAGC

CTGGGCTCCAATCAAGAAGAGGCCTACGTCACCATGAGCAGCTTCTAC

CAGAACCAG

Exemplary hinge sequence (SEQ ID NO: 5)
GAGCCTAAGAGCTGCGATAAGACCCACACCTGTCCTCCATGTCCTGAT Anti-CD123 scFv (SEQ ID NO: 6)
ATGGCCACAACCGACTGGATCTGGCGGATCCTGTTTCTTGTGGGAGCC

GCCACAGGCGCCCATTCTCAGGTTCAACTTCAGCAGCCTGGCGCCGAA

CTCGTTAGACCTGGCGCTTCTGTGAAGCTGAGCTGCAAGGCCAGCGGC

TACACCTTCACCAGCTACTGGATGAACTGGGTCAAGCAGAGGCCCGAC

CAGGGCCTCGAATGGATCGGAAGAATCGACCCCTACGACAGCGAGACA

CACTACAACCAGAAGTTCAAGGACAAGGCCATCCTGACCGTGGACAAG

AGCAGCAGCACAGCCTACATGCAGCTGAGCAGCCTGACCAGCGAAGAT

AGCGCCGTGTACTACTGCGCCAGAGGCAACTGGGATGACTATTGGGGC

CAGGGCACCACACTGACAGTTTCTAGCGGAGGCGGAGGTTCTGGTGGC

GGAGGAAGTGGCGGCGGAGGATCTGATGTGCAGATCACACAGAGCCCC

AGCTACCTGGCTGCATCTCCTGGCGAGACAATCACCATCAACTGCCGG

GCCAGCAAGAGCATCTCCAAGGACCTGGCCTGGTATCAAGAGAAGCCC

GGCAAGACCAACAAGCTGCTGATCTACAGCGGCAGCACACTGCAGTCT

GGCATCCCCAGCAGATTTTCCGGCTCTGGCAGCGGCACCGATTTCACC

CTGACCATAAGCTCCCTGGAACCTGAGGACTTCGCCATGTACTATTGC

CAGCAGCATAACAAGTACCCGTACACCTTCGGCGGAGGCACCAAGCTC

GAGATCAAG

---

The invention claimed is:

1. An engineered lymphocyte comprising a chimeric antigen receptor (CAR), the CAR comprising a single chain variable fragment (scFv) anti-CD123 antigen-recognition domain, an IL7Ra transmembrane domain, an IL7Ra intracellular signaling domain.

2. The engineered lymphocyte of claim 1, wherein the lymphocyte is a T cell.

3. The engineered lymphocyte of claim 1, wherein the lymphocyte is an NK cell.

4. The engineered lymphocyte of claim 1, wherein the CAR further comprises a hinge domain between the antigen-recognition domain and transmembrane domain.

5. The engineered lymphocyte of claim 1, wherein the lymphocyte further expresses a bispecific engager molecule comprising (a) a scFv antigen-recognition domain that specifically binds to C-type lectin-like molecule-1 (CLL-1); and (b) an anti-CD3 antibody fragment activation domain that interacts with a portion of T cell receptor (TCR) to induce an immunomodulatory signal.

6. The engineered lymphocyte of claim 5, wherein the activation domain and antigen-recognition domain are single chain variable fragments tethered to each other by a linker domain.

7. The engineered lymphocyte of claim 1, further comprising one or more linker segments between the domains.

8. A method of treating cancer in a subject comprising administering the engineered lymphocyte of claim 1 to the subject.

9. The method of claim 8, wherein the subject suffers from acute myeloid leukemia (AML).

* * * * *

SEQUENCE LISTING

Sequence total quantity: 6
SEQ ID NO: 1                moltype = AA   length = 459
FEATURE                    Location/Qualifiers
source                     1..459
                           mol_type = protein
                           organism = Homo sapiens
SEQUENCE: 1
MTILGTTFGM VFSLLQVVSG ESGYAQNGDL EDAELDDYSF SCYSQLEVNG SQHSLTCAFE    60
DPDVNTTNLE FEICGALVEV KCLNFRKLQE IYFIETKKFL LIGKSNICVK VGEKSLTCKK   120
IDLTTIVKPE APFDLSVIYR EGANDFVVTF NTSHLQKKYV KVLMHDVAYR QEKDENKWTH   180
VNLSSTKLTL LQRKLQPAAM YEIKVRSIPD HYFKGFWSEW SPSYYFRTPE INNSSGEMDP   240
ILLTISILSF FSVALLVILA CVLWKKRIKP IVWPSLPDHK KTLEHLCKKP RKNLNVSFNP   300
ESFLDCQIHR VDDIQARDEV EGFLQDTFPQ QLEESEKQRL GGDVQSPNCP SEDVVITPES   360
FGRDSSLTCL AGNVSACDAP ILSSSRSLDC RESGKNGPHV YQDLLLSLGT TNSTLPPPFS   420
LQSGILTLNP VAQGQPILTS LGSNQEEAYV TMSSFYQNQ                          459

SEQ ID NO: 2                moltype = DNA   length = 72
FEATURE                    Location/Qualifiers
source                     1..72
                           mol_type = genomic DNA
                           organism = Homo sapiens
SEQUENCE: 2
ccaatcctgc tgacaatcag catcctgagc tttttcagcg tggccctgct ggtcattctg    60

```
gccgtgctgt gg                                                                72

SEQ ID NO: 3              moltype = DNA   length = 72
FEATURE                   Location/Qualifiers
source                    1..72
                          mol_type = genomic DNA
                          organism = Homo sapiens
SEQUENCE: 3
ccaatcctgc tgataatcag catcctgagc tttttcagcg tggccctgct ggtcattctg   60
gccgtgctgt gg                                                                72

SEQ ID NO: 4              moltype = DNA   length = 585
FEATURE                   Location/Qualifiers
source                    1..585
                          mol_type = genomic DNA
                          organism = Homo sapiens
SEQUENCE: 4
aagaagcgga tcaagcctat cgtgtggccc agcctgcctg accacaaaaa gaccctggaa   60
cacctgtgca agaagccccg gaagaacctg aacgtgtcct tcaatcccga gagcttcctg  120
gactgtcaga ttcacagagt ggacgacatc caggccagag atgaggtgga aggctttctg  180
caggacacat tccctcagca gctggaagag agcgagaagc agagactcgg cggagatgtg  240
cagtccccta attgccctag cgaggacgtc gtgatcaacc ctgagagctt cggcagagat  300
agctccctga catgtctggc cggcaatgtg tccgcctgtg atgcccctat cctgagcagc  360
tccagaagcc tggattgcag agagagcggc aagaacggcc ctcacgtgta ccaagatctg  420
ctgctgagcc tgggcaccac caattctaca ctgcctccac cattcagcct gcagagcggc  480
atcctgacac tgaaccctgt tgctcagggc cagccaatcc tgacaagcct gggctccaat  540
caagaagagg cctacgtcac catgagcagc ttctaccaga accag               585

SEQ ID NO: 5              moltype = DNA   length = 48
FEATURE                   Location/Qualifiers
source                    1..48
                          mol_type = genomic DNA
                          organism = Homo sapiens
SEQUENCE: 5
gagcctaaga gctgcgataa gacccacacc tgtcctccat gtcctgat                         48

SEQ ID NO: 6              moltype = DNA   length = 777
FEATURE                   Location/Qualifiers
source                    1..777
                          mol_type = genomic DNA
                          organism = Homo sapiens
SEQUENCE: 6
atggccacaa ccgactggat ctggcggatc ctgtttcttg tgggagccgc cacaggcgcc   60
cattctcagg ttcaacttca gcagcctggc gccgaactcg ttagacctgg cgcttctgtg  120
aagctgagct gcaaggccag cggctacacc ttcaccagct actggatgaa ctgggtcaag  180
cagaggcccg accagggcct cgaatggatc ggaagaatcg acccctacga cagcgagaca  240
cactacaacc agaagttcaa ggacaaggcc atcctgaccg tggacaagag cagcagcaca  300
gcctacatgc agctgagcag cctgaccagc gaagatagcg ccgtgtacta ctgcgccaga  360
ggcaactggg atgactattg gggccagggc accacactga cagtttctag cggaggcgga  420
ggttctggtg gcggaggaag tggcggcgga ggatctgatg tgcagatcac acagagcccc  480
agctacctgg ctgcatctcc tggcgagaca atcaccatca ctgccgggc cagcaagagc  540
atctccaagg acctggcctg gtatcaagag aagcccggca agaccaacaa gctgctgatc  600
tacagcggca gcacactgca gtctggcatc cccagcagat tttccggctc tggcagcggc  660
accgatttca ccctgaccat aagctccctg gaacctgagg acttcgccat gtactattgc  720
cagcagcata acaagtaccc gtacaccttc ggcggaggca ccaagctcga gatcaag     777
```